US006428818B1

(12) United States Patent
Morré et al.

(10) Patent No.: US 6,428,818 B1
(45) Date of Patent: Aug. 6, 2002

(54) TEA CATECHIN FORMULATIONS AND PROCESSES FOR MAKING SAME

(75) Inventors: Dorothy M. Morré; D. James Morré, both of West Lafayette, IN (US); Raymond Cooper, Mountain View; Howard Sun, San Ramon, both of CA (US); Qing Ye, Shanghai (CN)

(73) Assignees: Purdue Research Foundation, West Lafayette, IN (US); Pharmanex, Inc., Brisbane, CA (US)

( * ) Notice: Subject to any disclaimer, the term of this patent is extended or adjusted under 35 U.S.C. 154(b) by 0 days.

(21) Appl. No.: 09/640,768

(22) Filed: Aug. 17, 2000

Related U.S. Application Data

(63) Continuation-in-part of application No. 09/537,211, filed on Mar. 29, 2000
(60) Provisional application No. 60/126,893, filed on Mar. 30, 1999, and provisional application No. 60/151,109, filed on Aug. 27, 1999.

(51) Int. Cl.[7] ............................................. A61K 35/78

(52) U.S. Cl. ................................................ 424/729

(58) Field of Search ........................................ 424/729

(56) References Cited

U.S. PATENT DOCUMENTS

| | | |
|---|---|---|
| 3,536,809 A | 10/1970 | Applezweig |
| 3,598,123 A | 8/1971 | Zaffaroni |
| 3,812,266 A * | 5/1974 | Sanderson et al. |
| 3,845,770 A | 11/1974 | Theeuwes et al. |
| 3,916,899 A | 11/1975 | Theeuwes et al. |
| 4,008,719 A | 2/1977 | Theeuwes et al. |
| 4,710,384 A | 12/1987 | Rotman |
| 4,891,231 A * | 1/1990 | Mai et al. |
| 5,059,595 A | 10/1991 | Le Grazie |
| 5,073,543 A | 12/1991 | Marshall et al. |
| 5,120,548 A | 6/1992 | McClelland et al. |
| 5,354,556 A | 10/1994 | Sparks et al. |
| 5,391,568 A | 2/1995 | Chung |
| 5,591,767 A | 1/1997 | Mohr et al. |
| 5,605,810 A | 2/1997 | Morré et al. |
| 5,639,476 A | 6/1997 | Oshlack et al. |
| 5,674,533 A | 10/1997 | Santus et al. |
| 5,733,566 A | 3/1998 | Lewis |
| 5,968,973 A | 10/1999 | Cheng et al. |
| 5,989,557 A | 11/1999 | Bombardelli et al. |
| 6,210,679 B1 | 4/2001 | Bailey et al. |

FOREIGN PATENT DOCUMENTS

| | | |
|---|---|---|
| EP | 0 819 433 A | 1/1998 |
| JP | 01268683 * | 10/1989 |
| JP | 05308901 * | 11/1993 |
| WO | WO 96/37201 A | 11/1996 |

OTHER PUBLICATIONS

Guo et al. Biochim. Biophys. Acta. 1996. vol. 1304, No. 3, pp. 210–222, Caplus abstract enclosed.*
Souquet et al. Bull. O.I.V. 2000, vol. 73 (835–836), pp. 601–609, Caplus abstract enclosed.*
Hashimoto et al.: "Tannins and Related Compounds. XC. 8–C–Ascorbyl(–)–Epigallocatechin3–O–Gallate and Novel Dimeric Flavan–3–ols, Oolonghomobisflavans A and B , from Oolong Tea. (3)" Chemical and Pharmaceutical Bulletin, JP, Pharmaceutical Society of Japan. Tokyo, vol. 37, No. 12, Dec. 1, 1989, pp. 3255–3263.
Nonaka et al.: "Tannins and Related Compounds. XV. A New Class of Dimeric Flavan–3–ol Gallates, Theasinensins A and B, and Proanthocyanadin Gallates from Geen Tea Leaf" Chemical and Pharmaceutical Bulletin, JP, Pharmaceutical Society of Japan. Tokyo, vol. 31, No. 11, 1983, pp. 3906–3914.
Wang et al. 1994. Inhibitory Effects of Black Tea, Green Tea, Decaffeinated Black Tea, and Decaffeinated Green Tea on Ultraviolet B Light–induced Skin Carcinogenesis in 7,12–Dimethylbenz[a]anthracene–initiated SKH–1 Mice. Cancer Research 54:3428–3435.
Aucamp j. et al. 1997. Inhibition of xanthine oxidase by catechins from tea (*Camellia sinensis*). Anticancer Res. 17(6D):4381–5.
Hirose M, et al. 1994. Inhibition of mammary gland carcinogenesis by green tea catechins and other naturally occurring antioxidants in female Sprague–Dawley rats pretreated with 7,12–dimethylbenz[alpha]anthracene. Cancer Lett. 83(1–2):149–56.
Saeki K. et al. 1999. Apoptosis–inducing activity of polyphenol compounds derived from tea catechins in human histiolytic lymphoma U937 cells. Biosci Biotechnol Biochem. 63(3):585–7.
Tanaka H. et al. 1997. Post–initiation inhibitory effects of green tea catechins on 7,12–dimethylbenz[a]anthracene–induced mammary gland carcinogenesis in female Sprague–Dawley rats. Cancer Lett.116(1):47–52.

(List continued on next page.)

*Primary Examiner*—Christopher R. Tate
(74) *Attorney, Agent, or Firm*—Pennie & Edmonds LLP

(57) ABSTRACT

The invention described herein encompasses methods and compositions of treating cancer or solid tumors comprising the administration of a therapeutically effective amount of catechins, a group of polyphenols found in green tea, to a mammal in need of such therapy. Compositions of catechins include but not limited to, epigallocatechin gallate (EGCg), epicatechin (EC), epicatechin gallate (ECG), epigallocatechin (EGC). The unique compositions of the invention contain various combinations of the catechins with reduced levels of EGCg, alone or in combination with each other or other therapeutic agents and are used to treat primary and metastatic cancers in humans. The invention also encompasses the varying modes of administration of the therapeutic compounds.

18 Claims, 20 Drawing Sheets

OTHER PUBLICATIONS

Figure 2A:
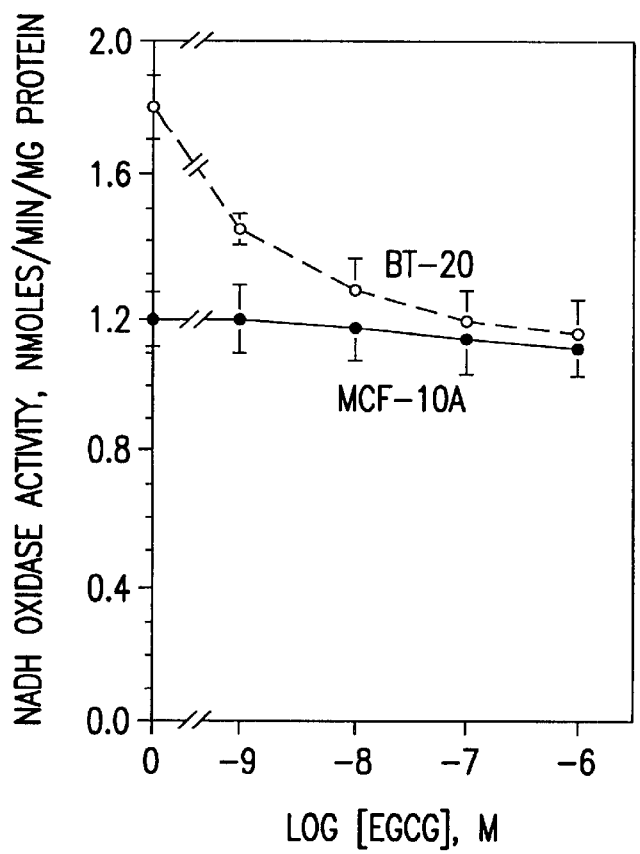

Ahmad et al., 1997, "Green tea constituent epigallocatechin–3–gallate and induction of apoptosis and cell cycle arrest in human carcinoma cells", J Natl Cancer Inst. 89(24):1881–6.

Ahmad et al., 1998, *Nutrition and Chemical Toxicity* (John Wiley and Sons, London) pp. 301–343.

Ahmad and Mukhtar, 1999, "Green tea polyphenols and cancer: biologic mechanisms and practical implications", Nutr Rev. 57(3):78–83.

Bridge et al., 1998, "Cancer–specific NADH oxidase (tNOX) a molecular target for the active principal of grean tea?", Mol. Biol. Cell 9:84A.

Brightman et al., 1992, "A growth factor– and hormone–stimulated NADH oxidase from rat liver plasma membrane", Biochim Biophys Acta. 1105(1):109–17.

Bruno et al., 1992, "Stimulation of NADH oxidase activity from rat liver plasma membranes by growth factors and hormones is decreased or absent with hepatoma plasma membranes", Biochem J. 284 (Pt 3):625–8.

Chan et al., 1997, "Inhibition of inducible nitric oxide synthase gene expression and enzyme activity by epigallocatechin gallate, a natural product from green tea", Biochem Pharmacol. 54(12):1281–6.

Chen et al., 1998, "Green tea epigallocatechin gallate shows a pronounced growth inhibitory effect on cancerous cells but not on their normal counterparts", Cancer Lett. 129(2):173–9.

Chueh et al., 1997, "A 33.5–kDa heat– and protease–resistant NADH oxidase inhibited by capsaicin from sera of cancer patients", Arch Biochem Biophys. 342(1):38–47.

Chueh et al., 1998, "Isolation and expression cloning of a tumor–associated NADH oxidase (tNOX) that is a potential pancancer maker", Mol. Biol. Cell 9:184A.

DeHahn et al., 1997, "NADH oxidase activity present on both the external and internal surfaces of soybean plasma membranes", Biochim Biophys Acta 1328:99–108.

del Castillo–Olivares et al., 1998, "A drug–responsive and protease–resistant peripheral NADH oxidase complex from the surface of HeLa S cells", Arch Biochem Biophys. 358(1):125–40.

Dong et al., 1997, "Inhibition of tumor promoter–induced activator protein 1 activation and cell transformation by tea polyphenols, (–)–epigallocatechin gallate, and theaflavins", Cancer Res. 57(19):4414–9.

Fujiki et al., 1998, "Cancer inhibition by green tea", Mutat Res. 402(1–2):307–10.

Gershoff, 1997, "Why green tea may help fight cancer", Tufts University Health and Nutrition Letter 15(6):2.

Katiyar et al., 1992, "(–)–Epigallocatechin–3–gallate in *Camellia sinensis* leaves from Himalayan region of Sikkim: inhibitory effects against biochemical events and tumor initiation in Sencar mouse skin", Nutr Cancer 18(1):73–83.

Khan et al., 1988, "Inhibition of the skin tumorigenicity of (+/–)–7 beta,8 alpha–dihydroxy–9 alpha,10 alpha–epoxy–7, 8,9,10–tetrahydrobenzo[a]pyrene by tannic acid, green tea polyphenols and quercetin in Sencar mice", Cancer Lett. 42(1–2):7–12.

Kishi et al., 1999, "The plasma membrane NADH oxidase of HeLa cells has hydroquinone oxidase activity", Biochim Biophys Acta 1412(1):66–77.

Komori et al., 1993, "Anticarcinogenic activity of green tea polyphenols", Jpn J Clin Oncol 23(3):186–90.

Kuroda and Hara, 1999, "Antimutagenic and anticarcinogenic activity of tea polyphenols", Mutat Res. 436(1):69–97.

Leff, 1999, "Rheumatoid arthritis caves in afflicted mice drinking down antioxidant green–tea extract", BioWorld Today, Apr. 16.

Liang et al., 1997, "Suppression of extracellular signals and cell proliferation through EGF receptor binding by (–)–epigallocatechin gallate in human A431 epidermoid carcinoma cells", J Cell Biochem. 67(1):55–65.

Liao et al., 1995, "Growth inhibition and regression of human prostate and breast tumors in athymic mice by tea epigallocatechin gallate", Cancer Lett. 96(2):239–43.

Lin and Lin, 1997, "(–)–Epigallocatechin–3–gallate blocks the induction of nitric oxide synthase by down–regulating lipopolysaccharide–induced activity of transcription factor nuclear factor–kappaB", Mol Pharmacol. 52(3):465–72.

Morre et al., 1996, "Capsaicin inhibits plasma membrane NADH oxidase and growth of human and mouse melanoma lines", Eur J Cancer 32A(11):1995–2003.

Morre et al., 1995, "Capsaicin inhibits preferentially the NADH oxidase and growth of transformed cells in culture", Proc Natl Acad Sci U S A. 92(6):1831–5.

Morre, 1994, "Hormone– and growth factor–stimulated NADH oxidase", J Bioenerg Biomembr. 26(4):421–33.

Morre, 1998, *Plasma Membrane Redox Systems and their Role in Biological Stress and Disease* (Klewer Academic Publishers, The Netherlands).

Morre et al., 1997, "Is the drug–responsive NADH oxidase of the cancer cell plasma membrane a molecular target for adriamycin?", J Bioenerg Biomembr. 29(3):269–80.

Morre and Brightman, 1991, "NADH oxidase of plasma membranes", J Bioenerg Biomembr. 23(3):469–89.

Morre et al., 1995, "The antitumor sulfonylurea N–(4–methylphenylsulfonyl)–N'–(4–chlorophenyl) urea (LY181984) inhibits NADH oxidase activity of HeLa plasma memrbanes", Biochim Biophys Acta. 1240(1):11–7.

Nakachi et al., 1998, "Influence of drinking green tea on breast cancer malignancy among Japanese patients", Jpn J Cancer Res. 89(3):254–61.

Paschka et al., 1998, "Induction of apoptosis in prostate cancer cell lines by the green tea component, (–)–epigallocatechin–3–gallate", Cancer Lett. 130(1–2):1–7.

Piazza et al., 1995, "Antineoplastic drugs sulindac sulfide and sulfone inhibit cell growth by inducing apoptosis", Cancer Res. 55(14):3110–6.

Robbins and Angell, 1976, *Basic Pathology, 2d Ed.* (W.B. Saunders Co., Philadelphia) pp. 68–79.

Roitt et al., 1993, *Immunology, $3^{rd}$ Ed.* (Mosby, St. Louis) pp. 17.1–17.12.

Ruch et al., 1989, "Prevention of cytotoxicity and inhibition of intercellular communication by antioxidant catechins isolated from Chinese green tea", Carcinogenesis 10(6):1003–8.

Sadzuka et al., "Modulation of cancer chemotherapy by green tea", Clin Cancer Res. 4(1):153–6.

Stoner and Mukhtar, 1995, "Polyphenols as cancer chemopreventive agents", J Cell Biochem Suppl. 22:169–80.

Suganuma et al., 1996, "A new process of cancer prevention mediated through inhibition of tumor necrosis factor alpha expression", Cancer Res. 56(16):3711–5.

Suganuma et al., 1998, "Wide distribution of [3H](–)–epigallocatechin gallate, a cancer preventive tea polyphenol, in mouse tissue", Carcinogenesis 19(10):1771–6.

Suganuma et al., 1999, "Synergistic effects of(--)-epigallocatechin gallate with (--)-epicatechin, sulindac, or tamoxifen on cancer-preventive activity in the human lung cancer cell line PC-9", Cancer Res. 59(1):44-7.

Sugiyama and Sadzuka, 1998, "Enhancing effects of green tea components on the antitumor activity of adriamycin against M5067 ovarian sarcoma", Cancer Lett. 133(1):19-26.

Sun et al., 1987, "NADH diferric transferrin reductase in liver plasma membrane", J Biol Chem. 262(33):15915-21.

Wang et al., 1989, "Protection against polycyclic aromatic hydrocarbon-induced skin tumor initiation in mice by green tea polyphenols", Carcinogenesis 10(2):411-5.

Weisburger, 1997, "Tea and health: a historical prespective", Cancer Lett. 114(1-2):315.

Wright et al., 1997, "Inhibition of apoptosis as a mechanism of tumor promotion", FASEB J. 8(9):654-60.

Yang et al., 1998, "Inhibition of growth and induction of apoptosis in human cancer cell lines by tea polyphenols", Carcinogenesis 19(4):611-6.

Edgren et al., 1991, "Controlled Release Technology (Pharmaceutical)", *Encyclopedia of Chemical Technology*, vol. 7, 4$^{th}$ edition (John Wiley and Sons, London) pp. 274-300.

Longer and Robinson, 1990, "Sustained-Release Drug Delivery Systems", *Remington's Pharmaceutical Sciences*, 18$^{th}$ edition (Mack Pub. Co., Easton, PA) pp. 1676-1693.

Nonaka et al., 1983, "Tannins and Related Compounds. XV. A New Class of Dimeric Flavan-3-ol Callates, Theasinensins A and B, and Proanthocyandin Gallates from Green Tea Leaf", Chem. Pharm. Bull. 31(11):3906-14.

Jackson and Lee, 1988, "Chemical Forms of Iron, Calcium, Magnesium and Zinc in Black, Oolong, Green and Instant Black Tea", J. Food Sci. 53(1): 181-4.

Horie et al., 1997, "Flow Injection Analysis of (-)-Epigallocatechin Gallate in Green Tea Infusions with Immobilized Tannase Reactor", Food Sci. Technol. Int. Tokyo 3(1):27-30.

Chen and Matsumoto, 1995, "Enzymatic Determination of gallotannin in green=Tea infusion by a photometric flowInjection analytical method", Anal. Sci. 11(5):777-80.

* cited by examiner

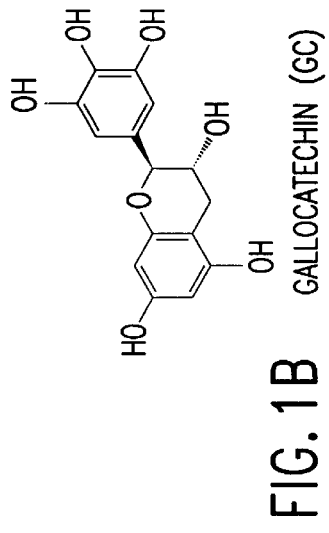
FIG. 1A EPICATECHIN (EC)
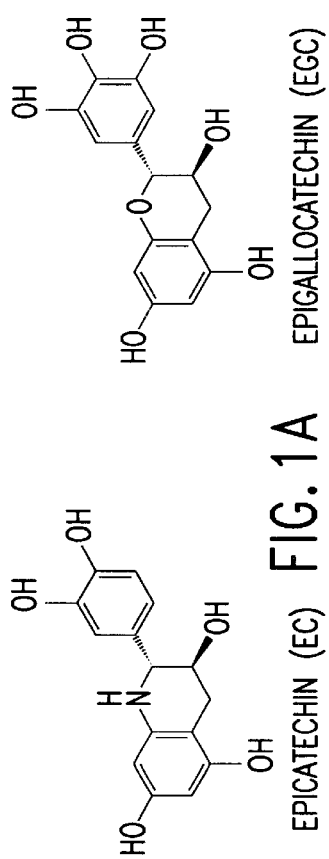
FIG. 1D EPICATECHIN GALLATE (ECG)
FIG. 1B EPIGALLOCATECHIN (EGC)
FIG. 1E EPIGALLOCATECHIN GALLATE (EGCg)
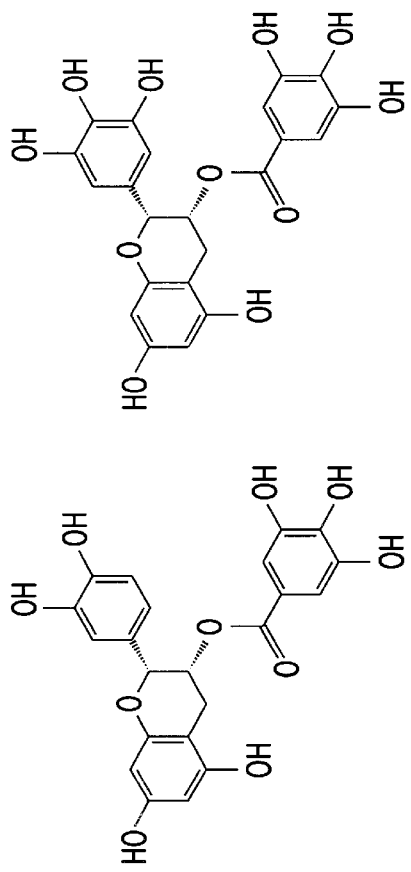
FIG. 1C GALLOCATECHIN (GC)
FIG. 1F GALLOCATECHIN GALLATE (GCG)
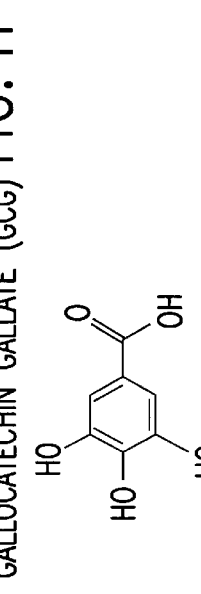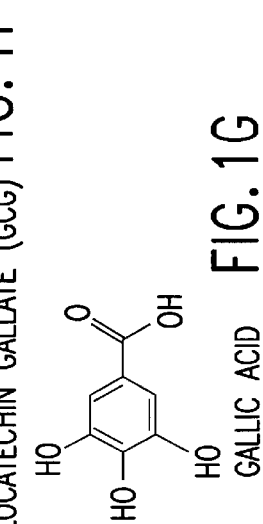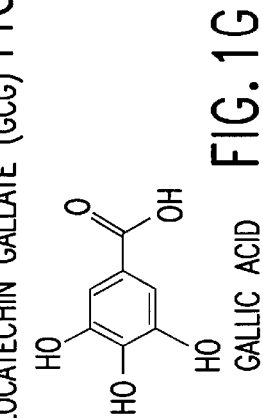
FIG. 1G GALLIC ACID

TEA CATECHIN FORMULATIONS AND PROCESSES FOR MAKING SAME

This application is a continuation-in-part of U.S. application Ser. No. 09/537,211, filed Mar. 29, 2000, which in turn claims benefit of U.S. provisional application serial No. 60/126,893, filed Mar. 30, 1999 and U.S. provisional application serial No. 60/151,109, filed Aug. 27, 1999.

1. INTRODUCTION

The present invention relates to novel compositions of catechins, including but not limited to, epigallocatechin gallate (EGCg), the major catechin in green tea leaves, epicatechin (EC), epicatechin gallate (ECG), and epigallocatechin (EGC), which are found in varying levels in tea leaves. The unique compositions of the invention contain various amounts of the catechins, including combinations of catechins, or catechins and other therapeutic agents, all of which contain significantly reduced levels of EGCg. The novel formulations are useful as dietary or nutritional supplements and therapeutics for the prevention and treatment of cancer. The present invention also encompasses methods of preparing compositions with reduced levels of EGCg.

2. BACKGROUND OF THE INVENTION

Tea is generally in the form of black, oolong, and green tea, all originating from the tea plant, *Camnellia sinensis*. Tea is cultivated in approximately thirty countries worldwide, and is consumed globally. Although the level of tea consumption varies around the world, it is believed that tea consumption is second only to water (Ahmad et al., 1998, Nutrition and Chemical Toxicity, John Wiley and Sons, Sussex, England, pp. 301–343). Black tea is consumed predominantly in Western and some Asian countries and green tea is consumed predominantly in China, Japan, India, and a few countries in North Africa and the Middle East (Ahmad et al., 1998, Nutrition and Chemical Toxicity, John Wiley and Sons, Sussex, England, pp. 301–343).

Green tea has been prized as a traditional tonic and has been widely consumed in East Asia. Recent studies have attempted to link green tea to antioxidant benefits including protection against the damage caused by cigarette smoke, pollution, stress, and other toxins (for an overview, see e.g., Mitscher, 1998, The Green Tea Book, Avery Publishing Group, Garden City Park, N.Y. and Weisburger, 1997, Can. Lett. 114:315–317).

An empirical link between green tea and its cancer prevention properties was made in the late 1980s (Khan et al., 1988, Can. Lett. 42:7–12 and Wang et al., 1989, Carcinogenesis 10:411–415). Epidemiological studies show that cancer onset of patients in Japan who had consumed ten cups of green tea per day was 8.7 years later among females and 3 years later among males, compared with patients who had consumed under three cups per day (Fujiki et al., 1998, Mutation Res. 402:307–310). As such, a possible relationship between high consumption of green tea and low incidence of prostate and breast cancer in Asian countries where green tea consumption is high has been postulated (Liao et al., 1995, Can. Lett. 96:239–243 and Stoner and Mukhtar, 1995, J. Cell. Biochem. 22:169–180). However, because of the many variables in lifestyle inherent to such a study, a definitive link between green tea and its cancer prevention effects could not be concluded.

Scientists have now identified many of the natural substances in green tea that may provide the majority of its health benefits. One class of chemicals that has attracted much study is the polyphenols, also known as catechins.

2.1. Epigallocatechin Gallate (EGCg)

The polyphenols describe a class of substituted phenolic compounds that are known as flavanols or catechins. The polyphenols in green tea that have been identified are catechin (C), epicatechin (EC), gallocatechin (GC), gallocatechin gallate (GCG), epigallocatechin (EGC), epicatechin gallate (ECG), and epigallocatechin gallate (EGCg) (FIG. 1). The typical percentage of the individual catechins in green tea extracts is 10–15% EGCg, 2–3% ECG, 2% EC, and 2–3% EGC (Suganuma et al., 1999, Can. Res. 59:44–47). In addition, caffeine, theobromine, theophylline, and phenolic acids, such as gallic acid, are also present as constituents of green tea in smaller quantities than the polyphenols (Ahmad et al., 1998, Nutrition and Chemical Toxicity, John Wiley and Sons, Sussex, England, pp. 301–343).

Epigallocatechin gallate (EGCg), the major catechin in green tea, has been the focus of many studies and is thought to be the primary active catechin. See the review article by Ahmad and Mukhtar, 1999, Nutr. Rev. 57:78–83. The administration of a pharmacologically effective amount of EGCg has been alleged to reduce the incidence of lung cancer in a mammal (U.S. Pat. No. 5,391,568). A bioavailability study showed that frequent green tea consumption results in high levels of EGCg in various body organs, suggesting that green tea consumption may protect against cancers localized to different sites of the body (Sugunama et al., 1998, Carcinogenesis 19:1771–1776).

EGCg has been implicated in blocking DNA transcription of a number of genes in cancer cell lines. For example, in the human epidermal carcinoma cell line A431, EGCg inhibits the DNA and protein synthesis of the growth factor receptors epidermal growth factor receptor (EGF-R), platelet-derived growth factor receptor (PDGF-R), and fibroblast growth factor receptor (FGF-R) (Liang et al., 1997, J. Cell. Biochem. 67:55–65). EGCg has also been implicated in blocking transcription of nitric oxide (NO) synthase by inhibiting the binding of transcription factor NFkB to the NO synthase promoter (Lin and Lin, 1997, Mol. Pharmacol. 52:465–472 and Chan et al., 1997, Biochem. Pharmacol. 54:1281–1286). In the tumor cell line JB6, EGCg inhibits AP-1 transcriptional activity (Dong et al., 1997, Can. Res. 57:4414–4419). These results suggest that EGCg may prevent cancer at the level of gene transcription, i.e., by blocking the DNA synthesis of genes involved in signal transduction pathways.

Further, the focus of many other studies has been the effect of EGCg on apoptosis, or programmed cell death. Apoptosis differs from necrosis, and is regarded as an ideal mechanism for the elimination of cells. Studies have shown that several anti-cancer preventative agents may induce apoptosis, and conversely, several tumor-promoting agents inhibit apoptosis (Wright et al., 1994, FASEB J 8:654–660 and Ahmad and Mukhtar, 1999, Nutr. Rev. 57:78–83).

Much of the prior work in the art has attempted to determine what, if any, effect EGCg has on the growth inhibition and apoptosis induction of cancer cells. A differential growth inhibitory effect was reported in human colorectal cancer cells Caco-2, breast cancer cells Hs578T, and their non-cancer cell counterparts (Ahinad and Mukhtar, 1999, Nutr. Rev. 57:78–83). EGCg has been implicated in the growth arrest and subsequent induction of apoptosis following cell growth inhibition has been shown in virally transformed fibroblast cells WI138, human epidermal carcinoma cells A431, lung cancer tumor cells H611, prostate cancer cell lines LNCaP, PC-3, and DU145, human carcinoma keratinocytes HaCaT, and mouse lymphoma cells LY-R (Chen et al., 1998, Can. Lett. 129:173–179; Ahrnad et al., 1997, J. Nat. Can. Inst. 89:1881–1886; Yang et al., 1998, Carcinogenesis 19:611–616; Paschka et al., 1998, Can. Lett. 130:1–7; and Ahmad and Mukhtar, 1999, Nutr. Rev. 57:78–83). In studies where the apoptotic response was studied in cancer cells versus their non-cancer counterparts, e.g., human carcinoma keratinocytes HaCaT versus normal human epidermal keratinocytes, the apoptotic response to EGCg was reported to be specific to the cancer cells (Ahmad et al., 1997, J. Nat. Can. Inst. 89:1881–1886).

It has been suggested that EGCg induced apoptosis may result from either cell cycle arrest and/or $H_2O_2$ production (Ahmad et al., 1997, J. Nat. Can. Inst. 89:1881–1886; Fujiki et al., 1998, Mutat. Res. 402:307–310; and Yang et al., 1998, Carcinogenesis 19:611–616). EGCg may be involved in the growth regulation of human epidermal carcinoma cells A431 by causing cell cycle arrest of the $G_0$ to $G_1$ phase (Ahmad et al., 1997, J. Nat. Can. Inst. 89:1881–1886). EGCg has also been implicated in phase arrest between $G_2$ to M phase of the cell cycle in human lung cancer cells (Fujiki et al., 1998, Mutat. Res. 402:307–310). In the EGCg induced inhibition of human lung cancer cells, it was suggested that the tumor necrosis factor (TNF) a pathway that is the mode of action of EGCg. Alternatively, the EGCg-induced apoptosis of the lung cancer tumor cells H611 is inhibited by catalase, suggesting the $H_2O_2$ production as a probable cause of apoptosis (Yang et al., 1998, Carcinogenesis 19:611–616).

2.2. Other Catechins and Combinations Thereof

Although the focus of much of the prior research has been on EGCg, the putative biological functions of some of the other catechins has been examined. For example, both epicatechin gallate (ECG) and epigallocatechin (EGC) have been reported to be as effective as EGCg in inducing apoptosis of human epidermal carcinoma cells A431 at similar concentrations, whereas epicatechin (EC) did not show a similar effect (Ahmad et al., 1997, J. of the Nat. Can. Inst. 89:1881–1886). Growth inhibition in lung tumor cell lines H661 and H1299 was also observed with EGCg and EGC, whereas ECG and EC were less effective (Yang et al., 1998, Carcinogenesis 19:611–616).

Catechins have been implicated in growth inhibition of the human lung cancer cell line PC-9, with the order of catechin potency being reported as EGCg= ECG>EGC>>>EC (Okabe et al., 1993, Jpn. J. Clin. Oncol. 23:186–190). It has also been demonstrated that catechin combinations of EGCg and EC, ECG and EC, and EGC and EC induce apoptosis of the human lung cancer cell line PC-9 in vitro (Suganuma et al., 1999, Can. Res. 59:44–47). EC is thought to enhance incorporation of EGCg into the cells, which is thought to inhibit TNF-α release resulting in the induction of apoptosis (Suganuma et al., 1999, Can. Res. 59:44–47).

Green tea extract has previously been reported to enhance the effect of the anti-cancer agents, e.g., adriamycin and doxorubicin (Sugiyama and Sadzuka, 1998, Can. Lett. 133:19–26 and Sadzuka et al., 1998, Clin. Can. Res. 4:153–156). Green tea in combination with adriamycin inhibits tumor growth in M5076 ovarian sarcoma cells, whereas adriamycin alone does not inhibit tumor growth in M5076 ovarian sarcoma cells (Sugiyama and Sadzuka, 1998, Can. Lett. 133:19–26). A similar effect is observed with green tea extract and doxorubicin on the same M5076 ovarian sarcoma cell line. Green tea extract, in combination with doxorubicin, also enhances the inhibitory growth effect on Ehrlich ascites carcinoma tumors in tumor-bearing mice, presumably by increasing the concentration of doxorubicin concentration in the tumor, but not in normal tissue (Sadzuka et al., 1998, Clin. Can. Res. 4:153–156).

EGCg has also been shown to enhance the effect of cancer prevention drugs in vitro. For example, EGCg has been shown to enhance the apoptotic effect of sulindac and tamoxifin, presumably by EGCg enhancing the intracellular concentration of the cancer prevention drugs. (Suganuma et al., 1999, Can. Res. 59:44–47). Both sulindac and tamoxifin induce apoptosis of human cancer cells and inhibit TNF-α release from BALB/c-3T3 cells (Piazza et al., 1995, Can. Res. 55:3110–3116; Chen et al., 1996, J. Cell. Biochem. 61:9–17; and Sugunama et al., 1996, Can. Res. 56:3711–3715).

Surprisingly, Applicants have discovered novel formulations of catechins with significantly reduced levels of EGCg are effective as dietary or nutritional supplements and therapeutics for the prevention and treatment of cancer.

2.3. NADH Oxidase

A unique plasma membrane NADH oxidase (NOX), a unique cell surface protein with hydroquinone (NADH) oxidase and protein disulfide-thiol interchange activities that is responsive to hormone and growth factors has been identified (Brightman et al., 1992, Biochim. Biophys. Acta 1105:109–117; Morré, 1994, J. Bioenerg. Biomemb. 26:421–433; and Morré, 1998, Plasma Membrane Redox Systems and their Role in Biological Stress and Disease, Klewer Academic Publishers, Dordrecht, The Netherlands, pp. 121–156). Further, a hormone-insensitive and drug-responsive form of NOX designated tNOX which is specific to cancer cells has been reported (Bruno et al., 1992, Biochem. J. 284:625–628; Morréand Morré, 1995, Protoplasma 184:188–195; Morréet al., 1995, Proc. Natl. Acad. Sci. U.S.A. 92;1831–1835; Morréet al., 1995, Biochim. Biophys. Acta 1240:11–17; Morréet al., 1996, Eur. J. Can. 32A:1995–2003; and Morréet al., 1997, J. Biomemb. Bioenerg. 29:269–280).

Because the NOX protein is located at the external plasma membrane surface and is not transmembrane, a functional role as an NADH oxidase is not considered likely (Morré, 1994, J. Bioenerg. Biomemb. 26:421–433; DeHahn et al., 1997, Biochim. Biophys. Acta 1328:99–108; and Morré, 1998, Plasma Membrane Redox Systems and Their Role in Biological Stress and Disease, Kiewer Academic Publishers, Dordrecht, The Netherlands, pp. 121–156). While the oxidation of NADH provides a basis for a convenient method to assay the activity, the ultimate electron physiological donor is most probably hydroquinones with specific activities for hydroquinone oxidation greater than or equal to that of NADH oxidation and/or protein thiol-disulfide interchange (Kishi et al., 1999, Biochim. Biophys. Acta 1412:66–77).

CNOX was originally defined as a drug-indifferent constitutive NADH oxidase activity associated with the plasma membrane of non-transformed cells that was the normal counterpart to tNOX (Morré, 1998, Plasma Membrane Redox Systems and Their Role in Biological Stress and Disease, Kiewer Academic Publishers, Dordrecht, The Netherlands, pp. 121–156). Indeed, a 36 kD protein isolated from rat liver and from plants has NOX activity that is unresponsive to tNOX inhibitors (Brightman et al., 1992, Biochim. Biophys. Acta 1105: 109–117).

While cancer cells exhibit both drug-responsive and hormone and growth factor-indifferent (tNOX) as well as drug inhibited and hormone and growth factor dependent (CNOX) activities, non-transformed cells exhibit only the drug indifferent hormone- and drug-responsive CNOX. Among the first descriptions of so-called constitutive or CNOX activity of non-transformed cells and tissues was where the activity of rat liver plasma membranes was stimulated by the growth factor, diferric transferrin (Sun et al., 1987, J. Biol. Chem. 262:15915–15921). Subsequent work demonstrated that the observed NADH oxidation was catalyzed by a unique enzyme exhibiting responsiveness to several hormones and growth factors (Bruno et al., 1992, Biochem J. 284:625–628). Unlike mitochondrial oxidases, the hormone-stimulated NADH oxidase activity of rat liver plasma membranes is not inhibited by cyanide (Morré, 1994, J. Bioenerg. Biomemb. 26: 421–433). The enzyme also was distinguished from other oxidase activities by its response to several common oxidoreductase inhibitors, e.g., catalase, azide and chloroquine, as well as to various detergents e.g., sodium cholate, Triton X-100 and CHAPS (Morré and Brightman, 1991, J. Bioenerg. Biomemb. 23:469–489 and Morré et al., 1997, J. Biomemb. Bioenerg. 29:269–280). Like tNOX of cancer cells, CNOX is a unique membrane-associated protein that is capable of oxidizing NADH but has an activity which is modulated by hormones and growth factors.

2.4. Pathobiology of Cancer

Cancer is characterized primarily by an increase in the number of abnormal cells derived from a given normal tissue, invasion of adjacent tissues by these abnormal cells, and lymphatic or blood-borne spread of malignant cells to regional lymph nodes and to distant sites (metastasis). Clinical data and molecular biologic studies indicate that cancer is a multistep process that begins with minor pre-neoplastic changes, which may under certain conditions progress to neoplasia.

Pre-malignant abnormal cell growth is exemplified by hyperplasia, metaplasia, or most particularly, dysplasia (for review of such abnormal growth conditions, see Robbins and Angell, 1976, Basic Pathology, 2d Ed., W. B. Saunders Co., Philadelphia, pp. 68–79) Hyperplasia is a form of controlled cell proliferation involving an increase in cell number in a tissue or organ, but without significant alteration in structure or function. As but one example, endometrial hyperplasia often precedes endometrial cancer. Metaplasia is a form of controlled cell growth in which one type of adult or fully differentiated cell substitutes for another type of adult cell. Metaplasia can occur in epithelial or connective tissue cells. Atypical metaplasia involves a somewhat disorderly metaplastic epithelium. Dysplasia is frequently a forerunner of cancer, and is found mainly in the epithelia; it is the most disorderly form of non-neoplastic cell growth, involving a loss in individual cell uniformity and in the architectural orientation of cells. Dysplastic cells often have abnormally large, deeply stained nuclei, and exhibit pleomorphism. Dysplasia characteristically occurs where there exists chronic irritation or inflammation, and is often found in the cervix, respiratory passages, oral cavity, and gall bladder.

The neoplastic lesion may evolve clonally and develop an increasing capacity for invasion, growth, metastasis, and heterogeneity, especially under conditions in which the neoplastic cells escape the host's immune surveillance (Roitt, Brostoff, and Kale, 1993, Immunology, 3rd ed., Mosby, St. Louis, pp. 17.1–17.12).

There remains a need for treatment of cancer that does not have the adverse effects generally caused by non-selectivity, of conventional chemotherapeutic agents. None of the above studies, which are not to be construed as an admission that any of the above studies is prior art, have suggested the present mechanism by which the catechins formulations with reduced levels of EGCg are able to differentiate between cancer and non-cancer cells. Moreover, none of the studies evaluated the efficacy of varying levels of catechin combinations or compositions of multiple catechins for the treatment of cancer. In contrast, the Inventors have identified a cancer-specific isoform of a unique plasma membrane NADH oxidase (tNOX) which is inhibited by the catechins. Furthermore, the studies cited supra have hypothesized that EGCg mediates its effects intracellularly, since EGCg incorporation into the cell seems to be a prerequisite for the inhibition of TNF-α release. Inhibition of tNOX, an extracellular membrane-associated protein) by EGCg, and synergistically with other catechins and anti-cancer agents, results in the selective inhibition of cancer cell growth and ultimately, apoptosis.

Surprisingly, applicants have discovered formulations having reduced levels of EGCg, such as formulations wherein EGCg is just 0.01%, 0.1%, 1.0%, 5% or 10% of the total catechins, are effective inhibitors of tNOX. Additionally, applicants have discovered formulations where the ratio of EC to EGCg is about 10:1, about 100:1, or about 1000:1 are effective inhibitors of tNOX.

3. SUMMARY OF THE INVENTION

The invention described herein encompasses formulations of catechins, a group of polyphenols found in green tea. Applicants have discovered catechin combinations containing surprisingly minute levels of EGCg which also effectively inhibit the activity of a cancer specific protein, an isoform of NADH oxidase specific to cancer cells (tNOX) and further effect cell growth.

In a specific embodiment, the catechin formulations comprise epigallocatechin gallate (EGCg), epicatechin gallate (ECG), epigallocatechin (EGC), and epicatechin (EC) or a combination thereof, optionally in combination with other polyphenols or other anti-cancer therapeutic agents.

In one embodiment, the catechin formulation contains about 0.01% of EGCg of the total catechins. In another embodiment, the catechin formulations contain about 0.1% of EGCg of the total catechins. In yet another embodiment, the catechin formulation contains about 1.0% of EGCg of the total catechins. In yet another embodiment, the catechin formulation contain about 5.0% of EGCg of the total catechins. In another embodiment, the catechin formulation contain less than 10% of EGCg of the total catechins.

In another embodiment, the ratio of EC to EGCg is about 10:1. In another embodiment, the ratio of EC to EGCg is about 100:1. In yet another embodiment, the ratio of EC to EGCg is about 1000:1.

The disclosure is based, in part, on the surprising discovery that minimal levels of epigallocatechin gallate (EGCg), in combination with other catechins, inhibit the activity of a cancer-specific protein, an isoform of NADH oxidase specific to cancer cells (tNOX). The invention provides a potent preventative and therapeutic effect on cancer cells without or while reducing the adverse effects on normal, healthy cells, while utilizing minimal levels of EGCg.

In a preferred embodiment, the invention encompasses methods of preparing novel catechin formulations containing significantly reduced levels of EGCg.

In accordance with the present invention, the catechin formulations with reduced levels of EGCg can be used alone or in combination with other known therapeutic agents or techniques to either improve the quality of life of the patient, or to treat cancer or solid tumors. The catechins can be used before, during, or after the administration of one or more known chemotherapeutic agents, including antitumor agents. In addition, the catechins can be used before, during, or after radiation treatment.

In another embodiment, the compositions of the invention are sterile pharmaceutical compositions suitable for intravenous injection or infusion. In another embodiment, the invention encompasses a composition suitable for oral delivery, comprising catechins and a pharmaceutically acceptable excipient or carrier. A preferred embodiment comprises a sustained release composition to maintain the circulating levels of said composition at a certain minimum level for therapeutic efficacy over a specified time period. Specific therapeutic regimens, pharmaceutical compositions, and kits are also provided by the invention.

The present invention includes methods of using the novel catechin formulations to treat and prevent cancer in mammals, preferably where the mammal is a human.

Particular compositions of the invention and their uses are described in the sections and subsections which follow.

3.1. Definitions

As used herein, the term "cancer" describes a diseased state in which a carcinogenic agent or agents causes the transformation of a normal cell into an abnormal cell, the invasion of adjacent tissues by these abnormal cells, and lymphatic or blood-borne spread of malignant cells to regional lymph nodes and to distant sites, i.e., metastasis.

As used herein, the terms "preventing cancer" and "prevention of cancer" mean to inhibit the transformation of a normal cell into an abnormal cell by a carcinogenic agent or agents and/or to inhibit the accumulation of cells expressing cancer-specific genes (e.g., tNOX) to a number which creates clinical symptoms associated with cancer.

As used herein, the terms "treating cancer" and "treatment of cancer" mean to inhibit the replication of cancer cells, to inhibit the spread of cancer, to decrease tumor size, to lessen or reduce the number of cancerous cells in the body, and to ameliorate or alleviate the symptoms of the disease caused by the cancer. The treatment is considered therapeutic if there is a decrease in mortality and/or morbidity.

The term "synergistic" as used herein refers to a combination which is more effective than the additive effects of any two or more single agents. A determination of a synergistic interaction between catechins, and another therapeutic agent may be based on the results obtained from the NOX assays described in Section 5.4 infra. The results of these assays are analyzed using Chou and Talalay's combination method and Dose-Effect Analysis with Microcomputers' software in order to obtain a Combination Index (Chou and Talalay, 1984, Adv. Enzyme Regul. 22:27–55 and Chou and Chou, 1987, software and manual, Elsevier Biosoft, Cambridge, UK, pp. 19–64). Combination Index values<1 indicates synergy, values>1 indicate antagonism and values equal to 1 indicate additive effects.

The terms "pharmaceutically acceptable carrier" and "ingestable carrier" refer to a carrier medium that does not interfere with the effectiveness of the biological activity of the active ingredient, is chemically inert and is not toxic to the patient to whom it is administered.

The term "pharmaceutically acceptable salts" refers to salts prepared from pharmaceutically acceptable non-toxic acids and bases, including inorganic and organic acids and bases.

As used herein, the term "pharmaceutically acceptable derivative" refers to any homolog, analog, or fragment corresponding to the catechin formulations as described in Section 5.1 infra which exhibits anti-cancer activity and is relatively non-toxic to the subject.

The term "therapeutic agent" refers to any molecule, compound or treatment that assists in the treatment of a cancer or the diseases caused thereby.

As used herein, the term "reduced levels of EGCg" refers to either catechin formulations which have concentrations of EGCg of less than green tea extract and generally less than 10% and preferably less than 1.0% or catechin formulations where the ratio of EC to EGCg is at least 10:1, preferably 100:1, up to about 1000:1

The catechins and target proteins defined herein are abbreviated as follows:

| | |
|---|---|
| (±) - catechin | C |
| (−) - epicatechin | EC |
| (−) - epicatechin gallate | ECG |
| gallocatechin | GC |
| gallocatechin gallate | GCG |
| (−) - epigallocatechin | EGC |
| (−) - epigallocatechin gallate | EGCg |
| nicotinamide adenine dinucleotide | NADH |
| cell surface hydroquinone (NADH) oxidase with protein disulfide - thiol isomerase activity | NOX |
| NOX present in both non-cancer and cancer cells | CNOX |
| NOX specific to cancer cells | tNOX |

4. BRIEF DESCRIPTION OF THE DRAWINGS

FIGS. 1A–1G. Structures of six catechins from green tea. A. (±)-catechin (C). B. (−)-epicatechin (EC). C. (−)-epigallocatechin (EGC). D. (−)-epicatechin gallate (ECG). E. (−)-epigallocatechin gallate (EGCg). F. (−)-gallocatechin gallate (GCG)

FIGS. 2A–2D. Dose-response of NADH oxidase of isolated plasma membranes (A, B) and growth of attached cells (C, D) to (−)-epigallocatechin gallate (EGCg). A, C. MCF-10A human mammary epithelial (non-cancer) cells (●) and BT-20 human mammary adenocarcinoma (cancer) cells (○). B, D. HeLa (human cervical carcinoma) cells. Values are averages of duplicate determinations in each of three separate experiments (n=6)±standard deviations among experiments (n=3).

Figure 2B:
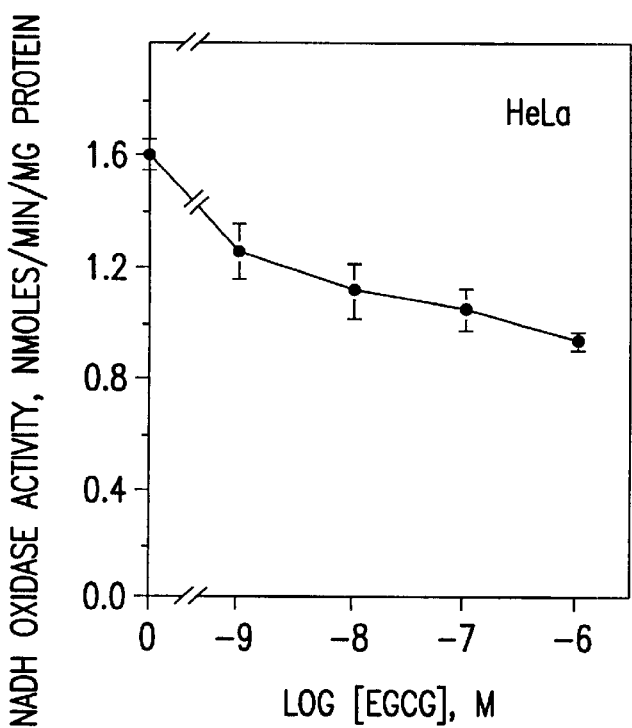
Figure 2C:
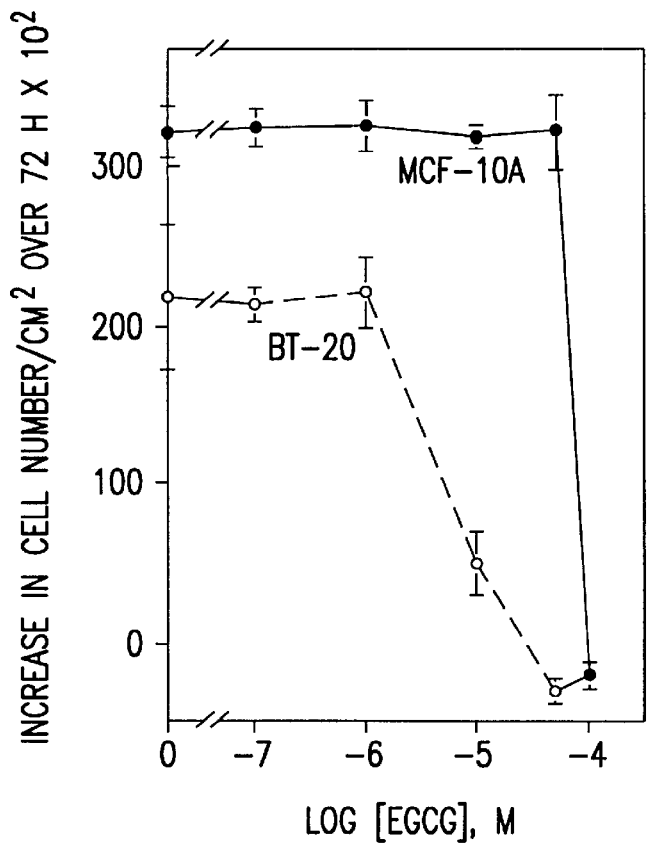
Figure 2D:
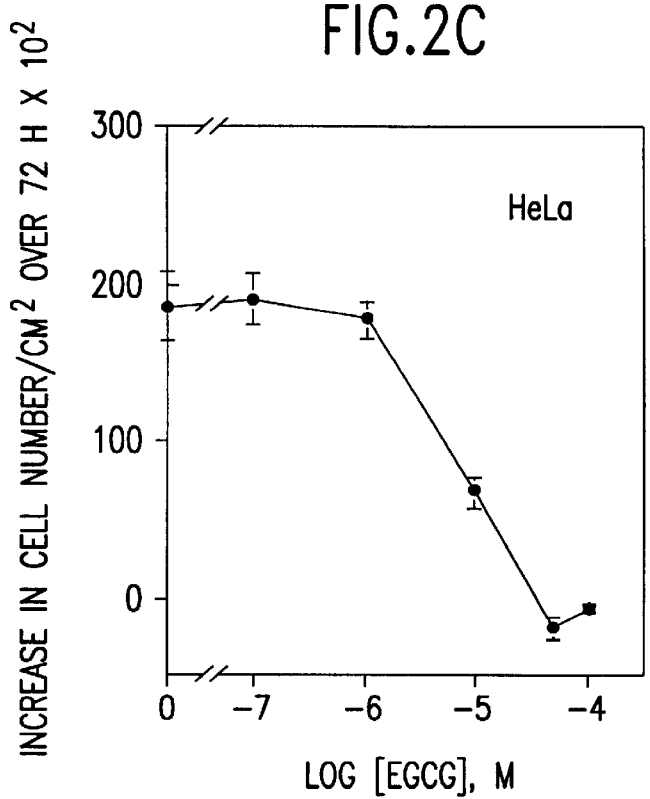
Figure 3B:
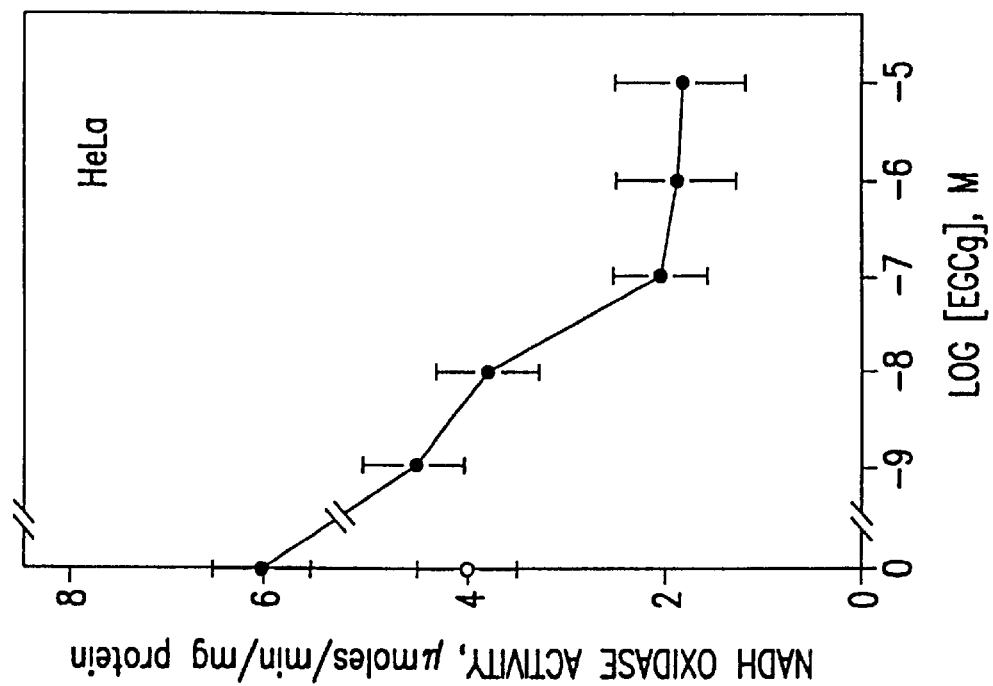
Figure 3A:
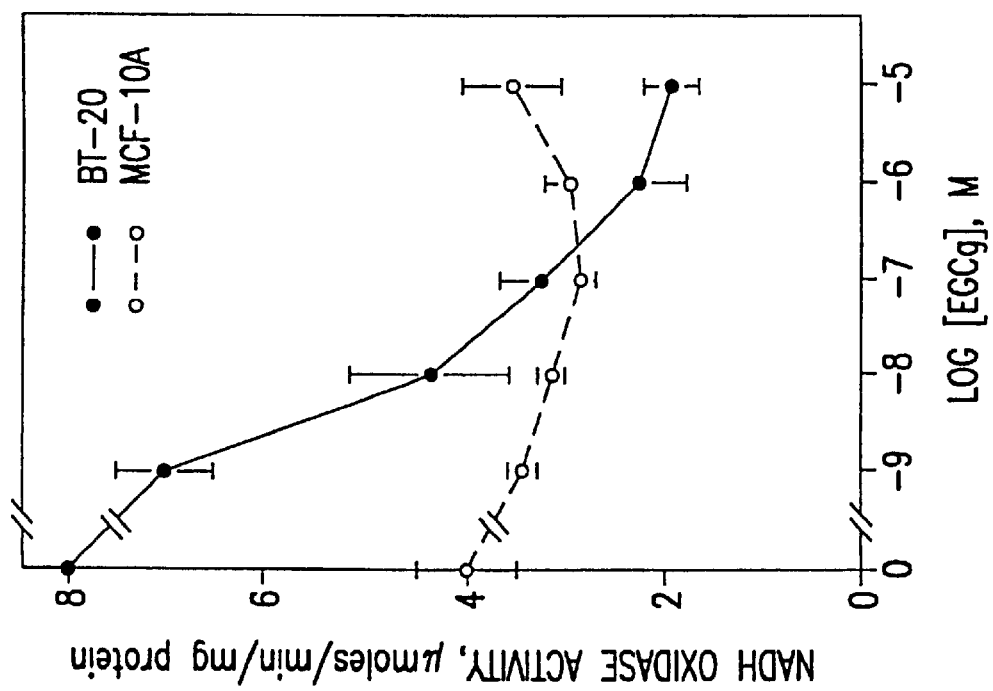

FIGS. 3A–3B. Dose-response of solubilized and partially purified NADH oxidase to (−)-epigallocatechin gallate (EGCg). A. NADH oxidase from MCF-10A and BT-20 cells. B. NADH oxidase from HeLa cells. As with plasma membranes (FIG. 2), the preparations from BT-20 and HeLa cells contained NOX activities both susceptible and resistant to inhibition by EGCg whereas the preparations from MCF10A cells was resistant to inhibition. Results are averages of duplicate determinations in each of three separate experiments (n=6)±standard deviations among experiments (n=3).

Figure 4:
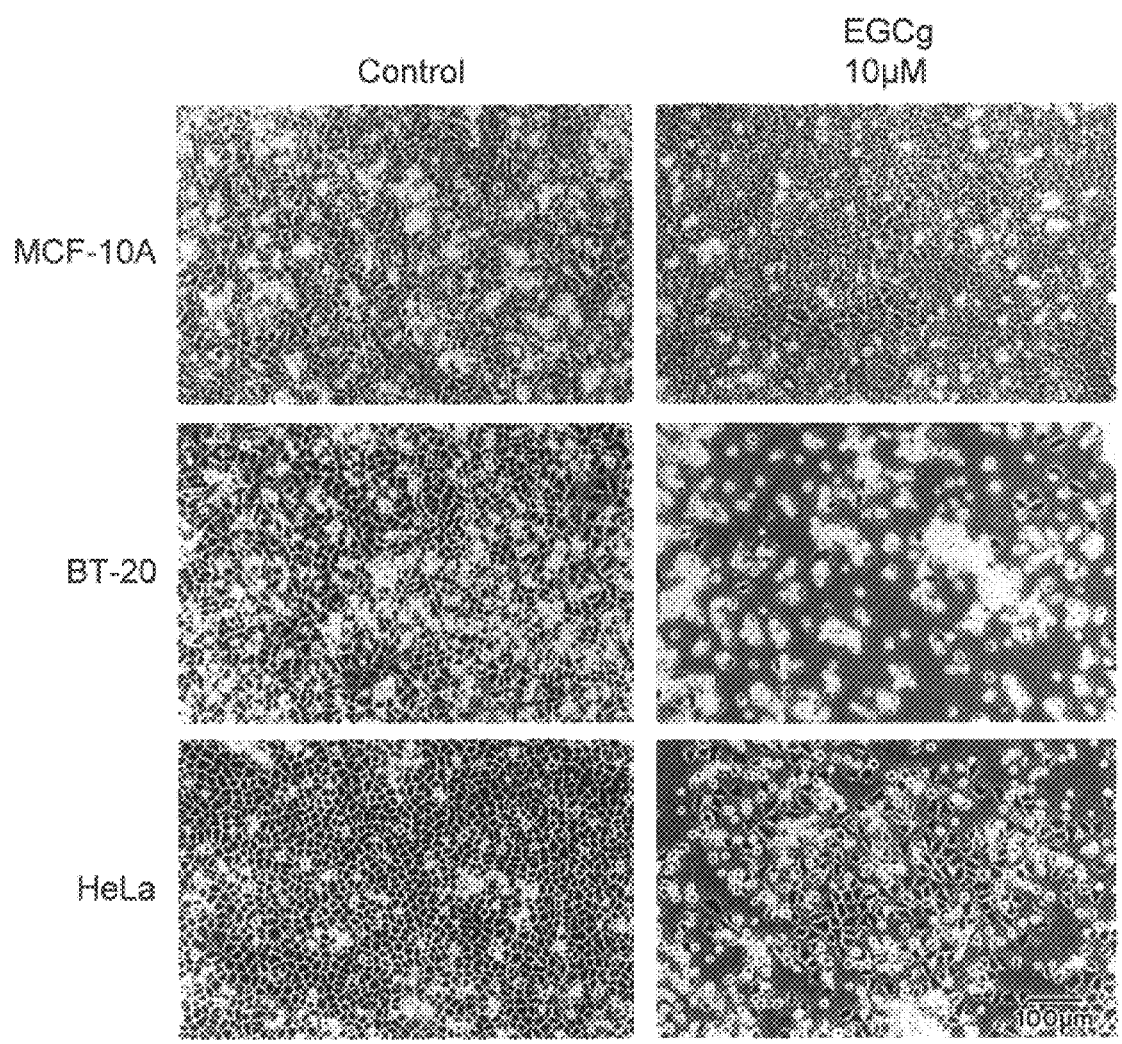

FIG. 4. Photomicrographs of MCF-10A mammary epithelial (non-cancer), BT-20 mammary adenocarcinoma and HeLa cells treated for 96 h with 10 mM (−)-epigallocatechin gallate (EGCg) added at t=0. The BT-20 and HeLa cells stopped growing and died whereas the MCF-10 cells recovered fully.

Figure 5:
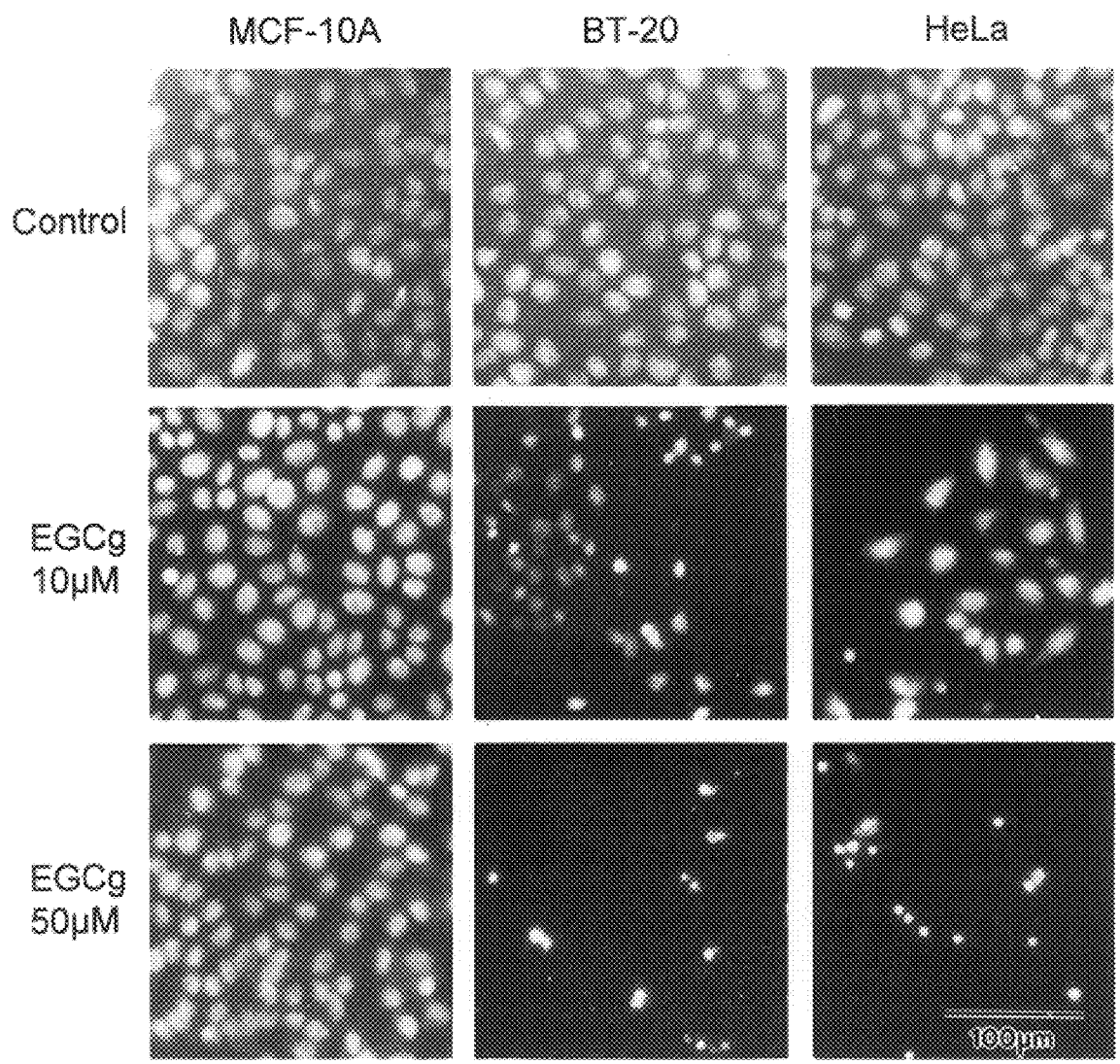

FIG. 5. Photomicrographs of MCF-10A, BT-20 and HeLa cells stained with 4',6-diamidino-2-phenylindole (DAPI) (Wolvetang et al., 1994, FEBS Lett. 339:40–44) to show condensed chromatin after 96 h in the presence of 10 or 50 mM epigallocatechin gallate (EGCg) characteristic of apoptosis for BT-20 and HeLa but not for MCF-10A cells. Cells were grown on coverslips in the absence (upper panel) or presence (lower 2 panels) of 10 or 50 mM EGCg and fixed. Nuclear DNA was stained with DAPI and analyzed with a fluorescence microscope.

Figure 6:
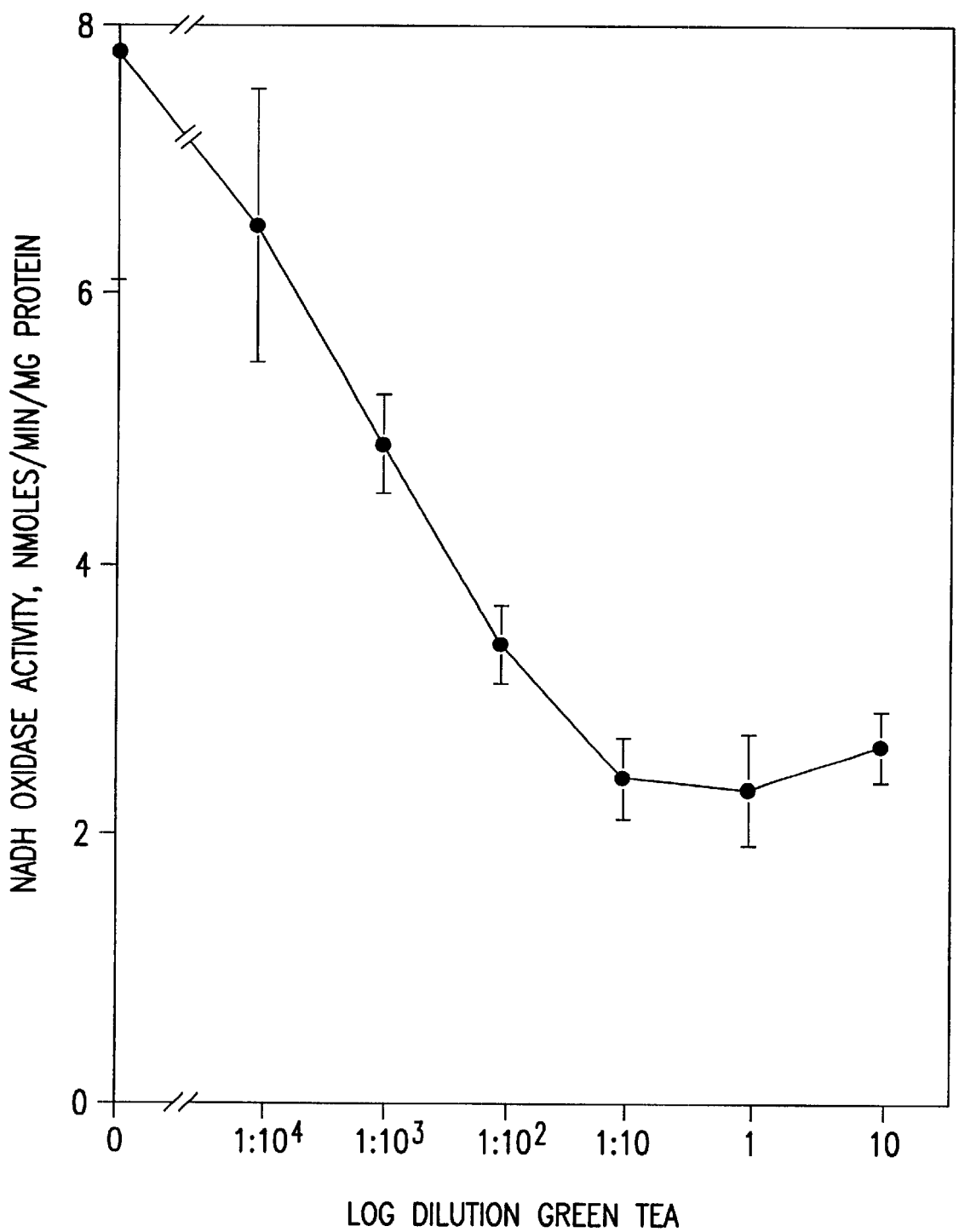

FIG. 6. Inhibition of partially purified tNOX from HeLa cells by green tea infusions. The $EC_{50}$ for inhibition of the enzymatic activity was at a tea dilution of about 1:1000. The preparations contained an activity resistant to inhibition as well so that the inhibition by the tea infusions was not complete and further inhibition by green tea was not observed above a dilution of about 1:10. Results are averages of duplicate determinations in each of three separate experiments (n=6)±standard deviations among experiments (n=3).

Figure 7:
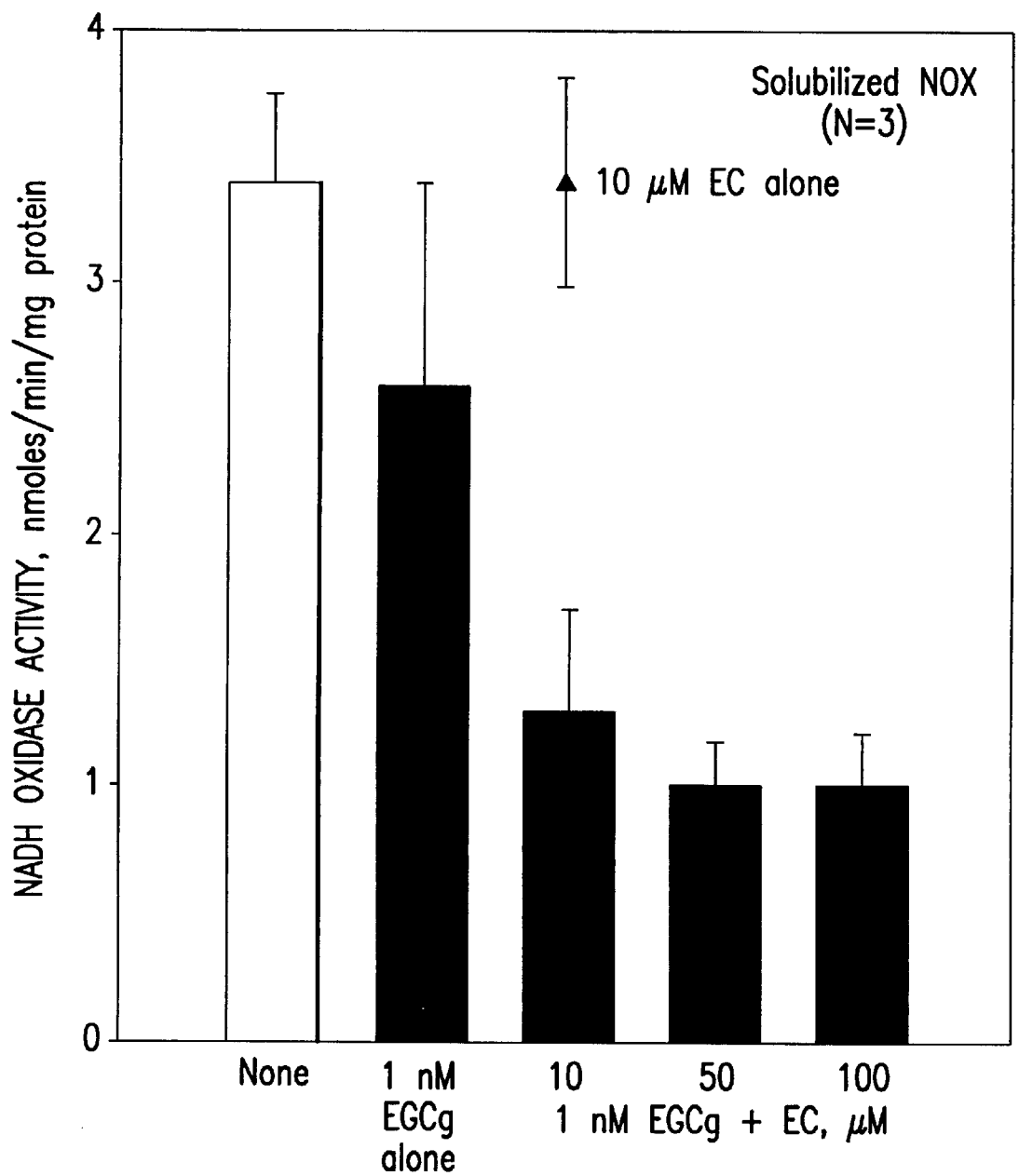

FIG. 7. Response of the NADH oxidase activity solubilized and partially purified as described from plasma membrane vesicles of HeLa cells to 1 nM (-)-epigallocatechin gallate (EGCg) alone and in combination with (-)-epicatechin (EC) at 10, 50 and 100 mM (del Castillo et al, 1998, Arch. Biochem. Biophys. 358:125–140). Values are from duplicate determinations from each of three different experiments±standard deviations. HeLa cells contain NOX activities containing both a drug-susceptible component (tNOX, 40 to 60% of the total) and a drug-resistant component (CNOX, 40 to 60%) of the total. The effect of EC in the presence of 1 nM EGCg alone is to inhibit completely the tNOX component without an effect on CNOX activity.

Figure 8:
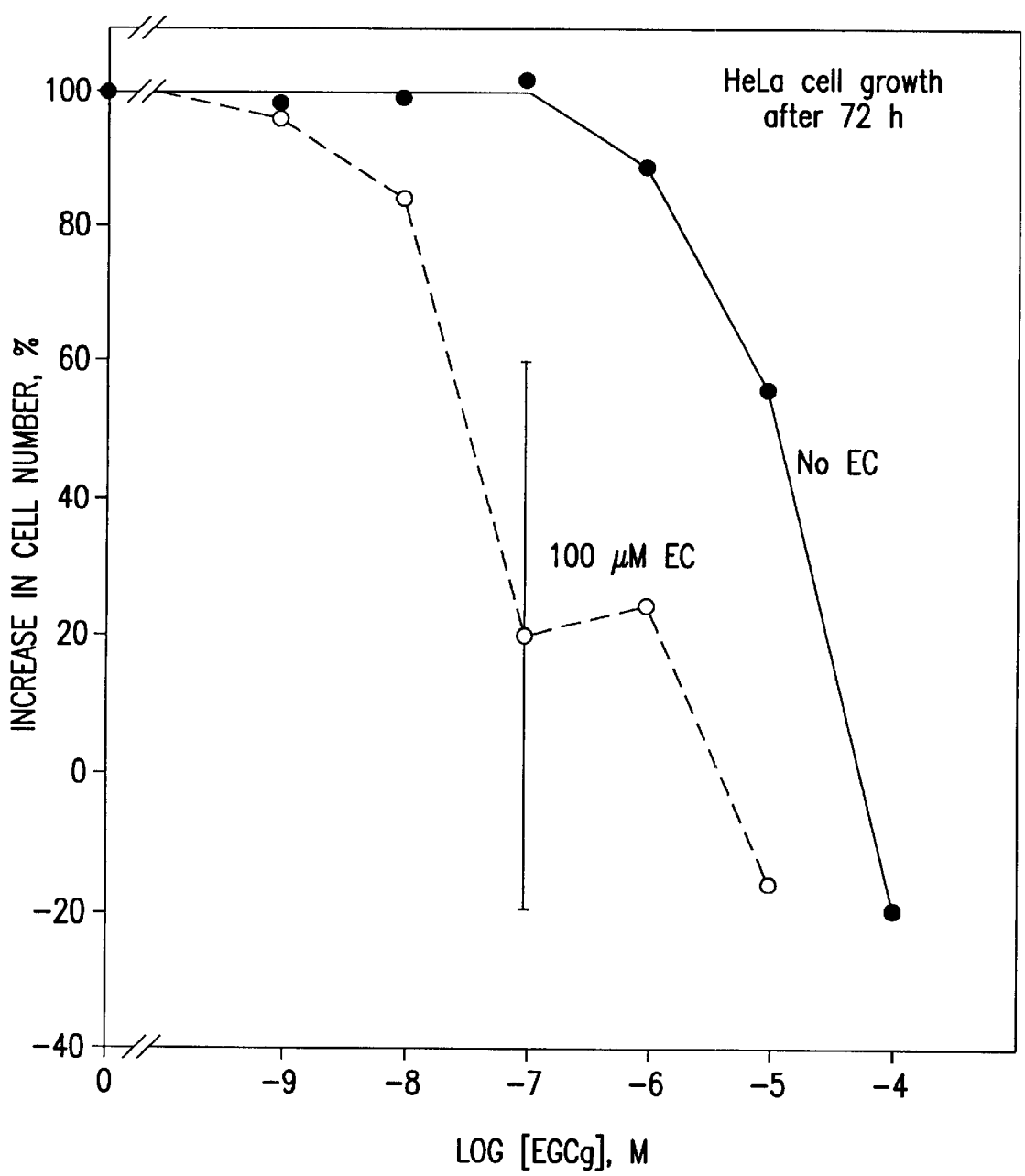

FIG. 8. Dose response of the growth of HeLa cells after 72 h to (-)-epigallocatechin (EGCg) in the absence or presence of 100 mM (-)-epicatechin (EC). Values are from duplicate determinations from single experiments except for $10^{-7}$ M EGCg which is the average of duplicate determinations from 3 experiments±standard deviations.

Figure 9:
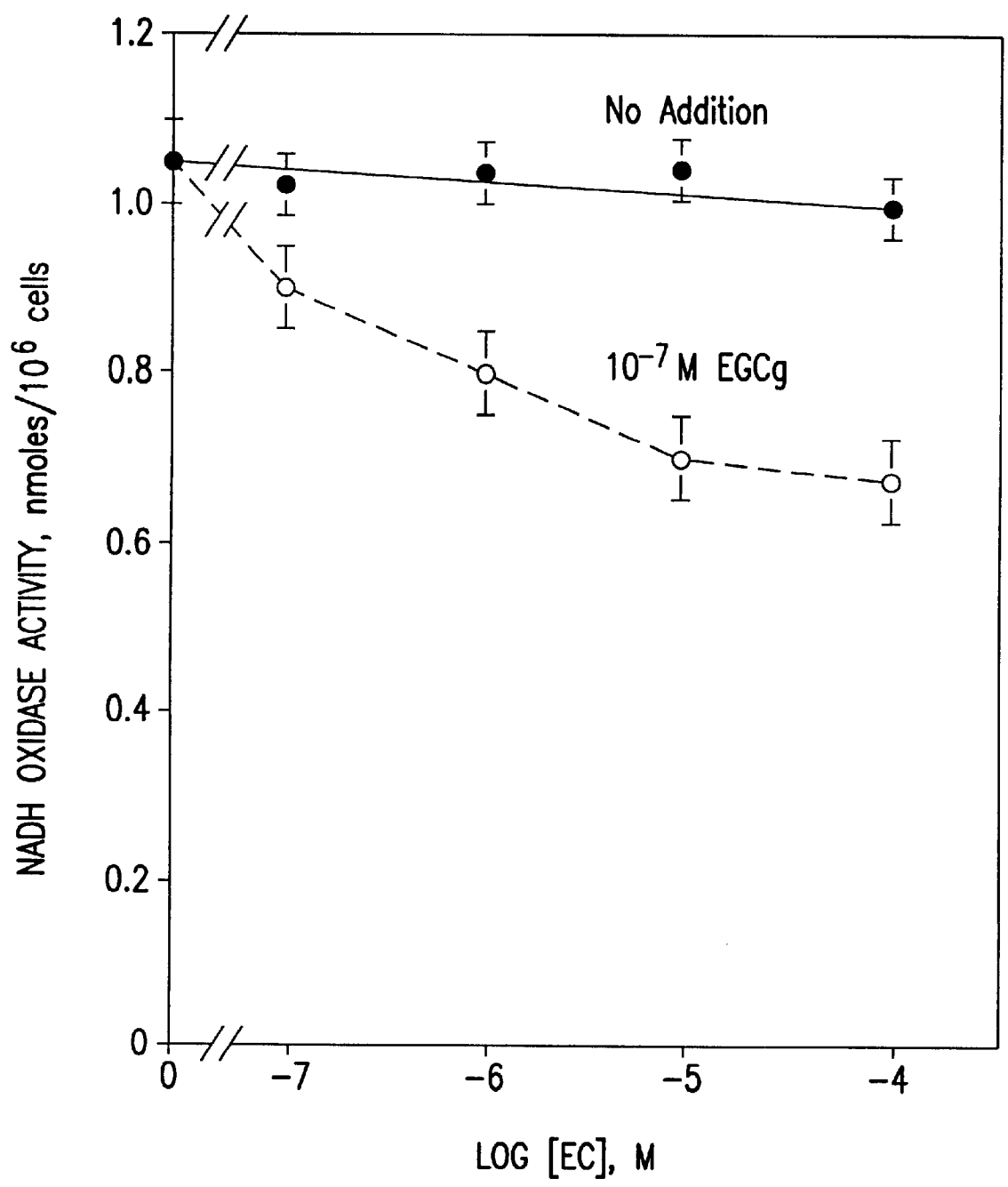

FIG. 9. Response of the NADH oxidase of 4T1 mouse mammary cells to (-)-epicatechin (EC) alone (upper curve, solid symbols) or in the presence of $10^{-7}$ M (-)-epigallocatechin gallate (EGCg) (lower curve, open symbols, dashed line). The tNOX activity (see FIG. 12) was completely inhibited by $10^{-4}$ M EC in the presence of 0.1 mM EGCg without effect on CNOX activity. Values are averages of 3 experiments±standard deviations.

Figure 10:
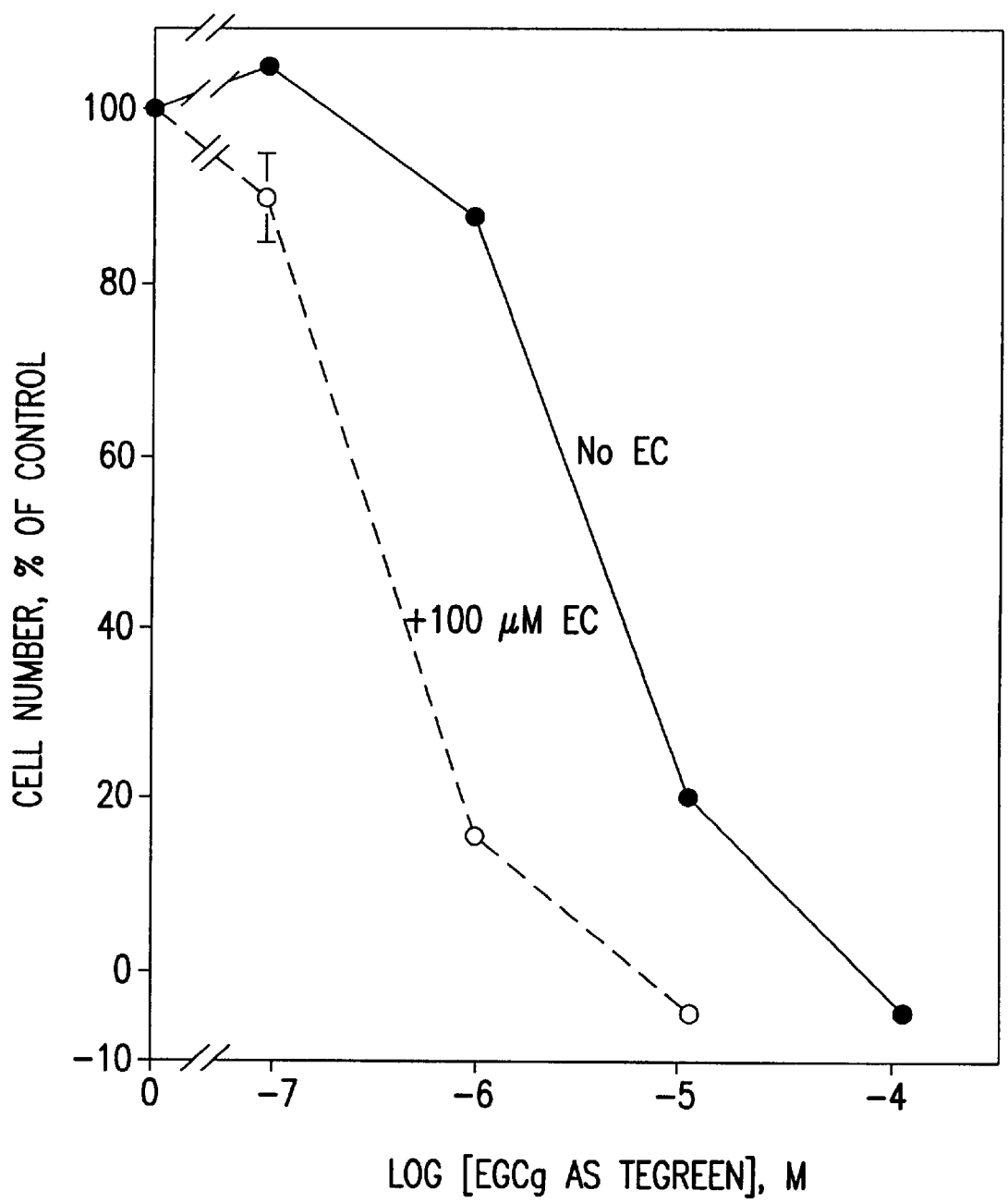

FIG. 10. Dose response of the growth of 4T1 cells after 72 h to (-)-epigallocatechin gallate (EGCg) provided in combination with other tea catechins as Tegreen™ in the absence or presence of 100 mM (-)-epicatechin (EC). Values are from duplicate determinations from single experiments except for $10^{-7}$ M EGCg which is the average of duplicate determinations from 3 experiments±standard deviations.

Figure 11:
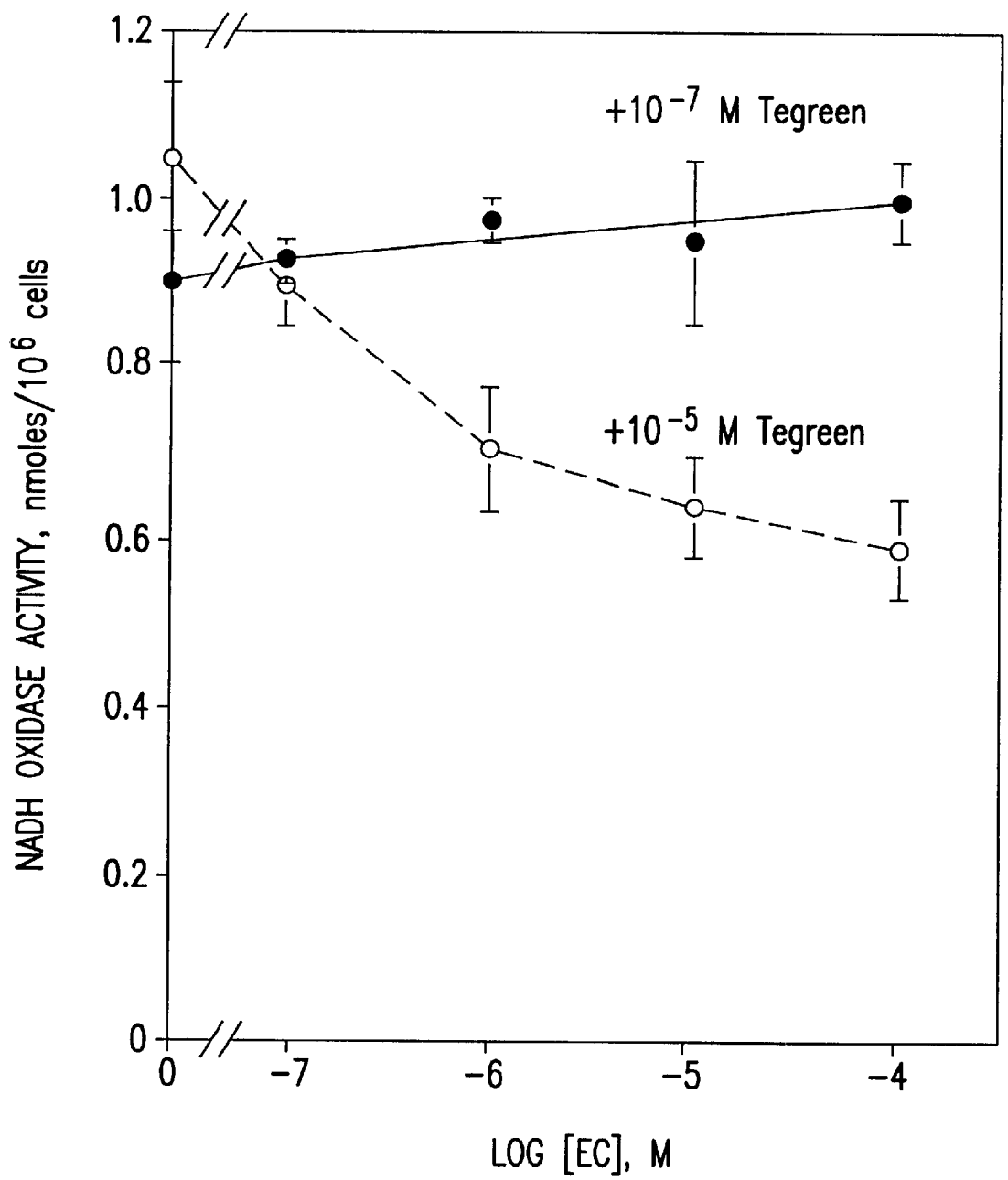

FIG. 11. Response of the NADH oxidase of 4T1 mouse mammary cells to (-)-epicatechin (EC) in the presence of $10^{-7}$ M Tegreen™ (upper curve, solid symbols) or $10^{-5}$ M Tegreen™ (lower curve, open symbols, dashed line). The tNOX activity (see FIG. 12) was completely inhibited by $10^{-4}$ M EC in the presence of 0.1 mM EGCg without effect on CNOX activity. Values are averages of 3 experiments±standard deviations.

Figure 12:
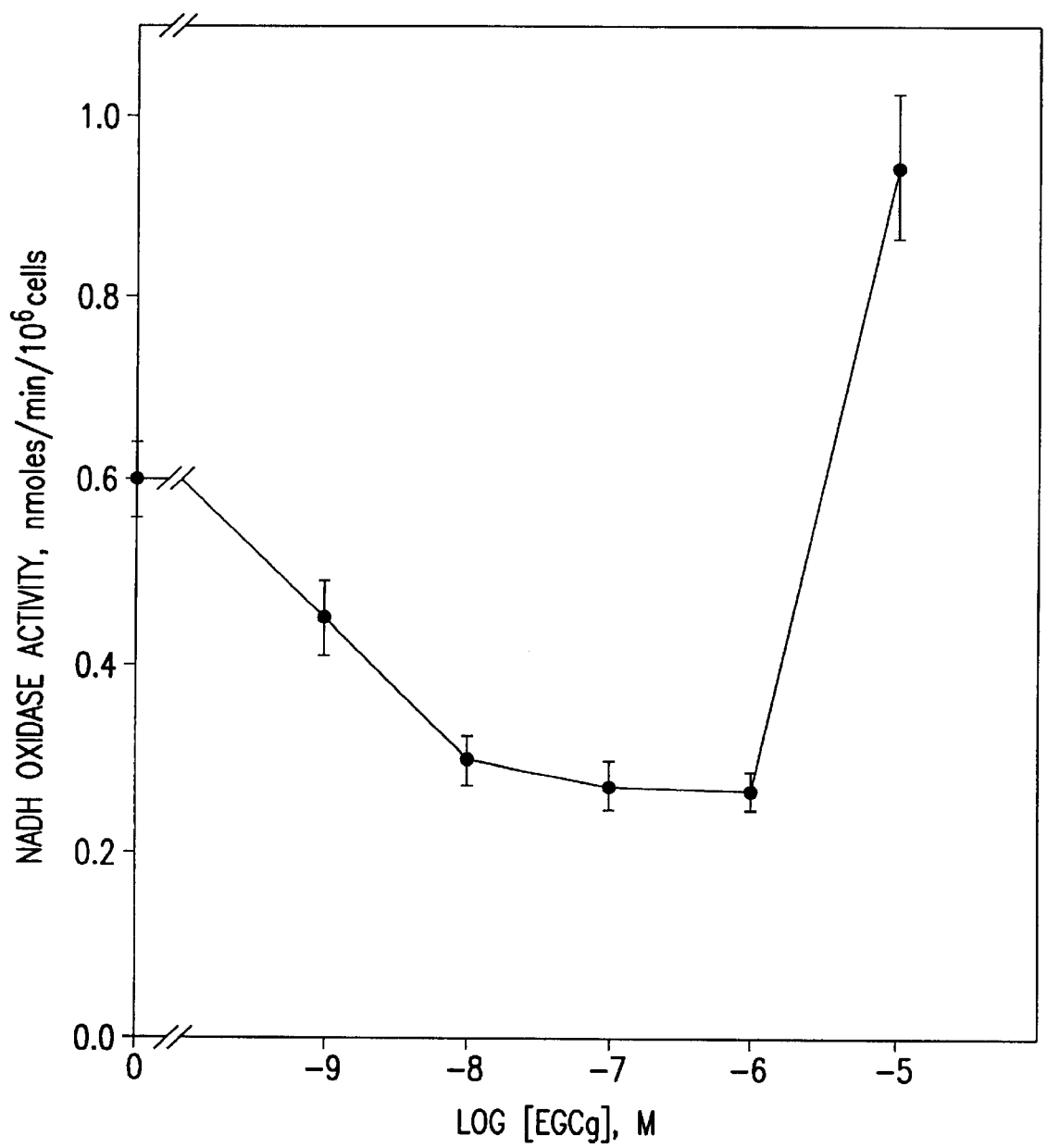

FIG. 12. Response of the NADH oxidase of HeLa S cells to (-)-epigallocatechin gallate (EGCg) alone. The tNOX activity was maximally inhibited by 0.1 mM EGCg without effect on CNOX activity. Values are averages of 3 experiments±standard deviations.

Figure 13:
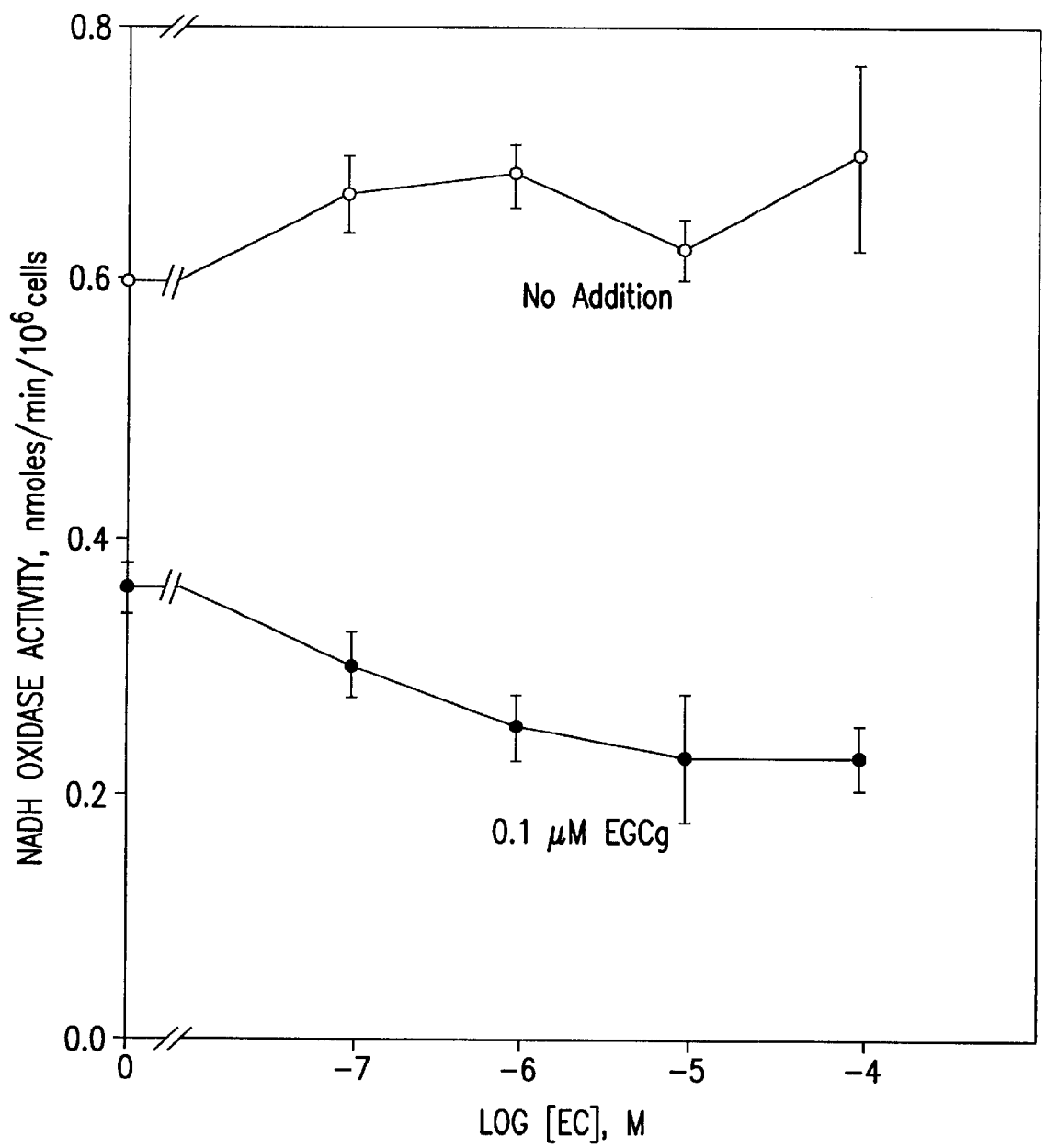

FIG. 13. Response of the NADH oxidase of HeLa S cells to (-)-epicatechin (EC) alone (upper curve, solid symbols) or in the presence of $10^{-7}$ M epigallocatechin gallate (EGCg) (lower curve, open symbols, dashed line). The tNOX activity was completely inhibited by $10^{-4}$ M EC in the presence of 0.1 mM EGCg without effect on CNOX activity. Values are averages of 3 experiments±standard deviations.

Figure 14:
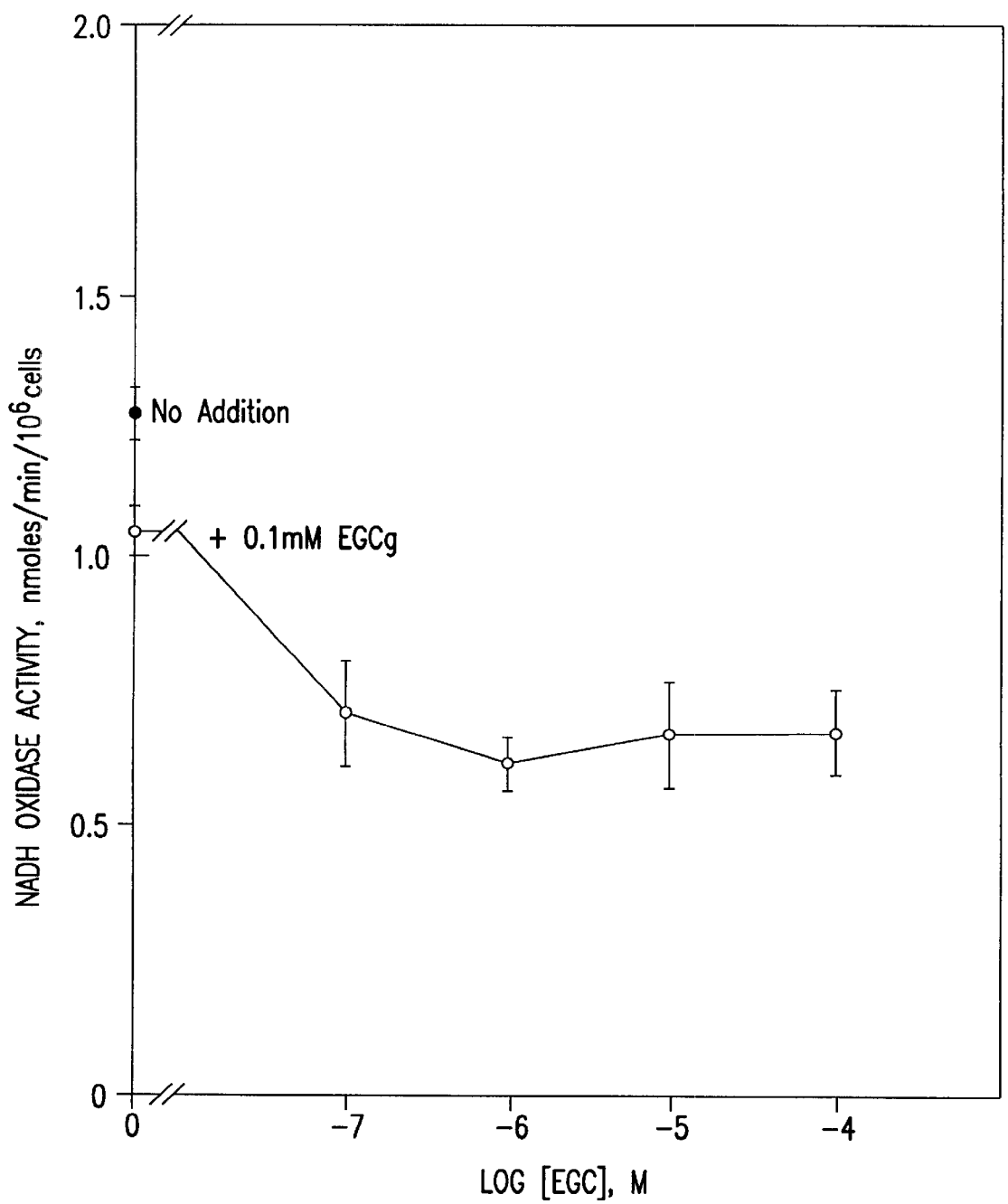

FIG. 14. Response of the NADH oxidase of 4T1 mouse mammary cells to varying concentrations of (-)-epicatechin gallate (ECG) alone or in the presence of $10^{-7}$ M (-)-epigallocatechin gallate (EGCg). The tNOX activity was completely inhibited by $10^{-6}$ M EC in the presence of 0.1 mM EGCg without effect on CNOX activity. Values are averages of duplicate determinations from 2 experiments±mean average deviations between the two experiments.

Figure 15:
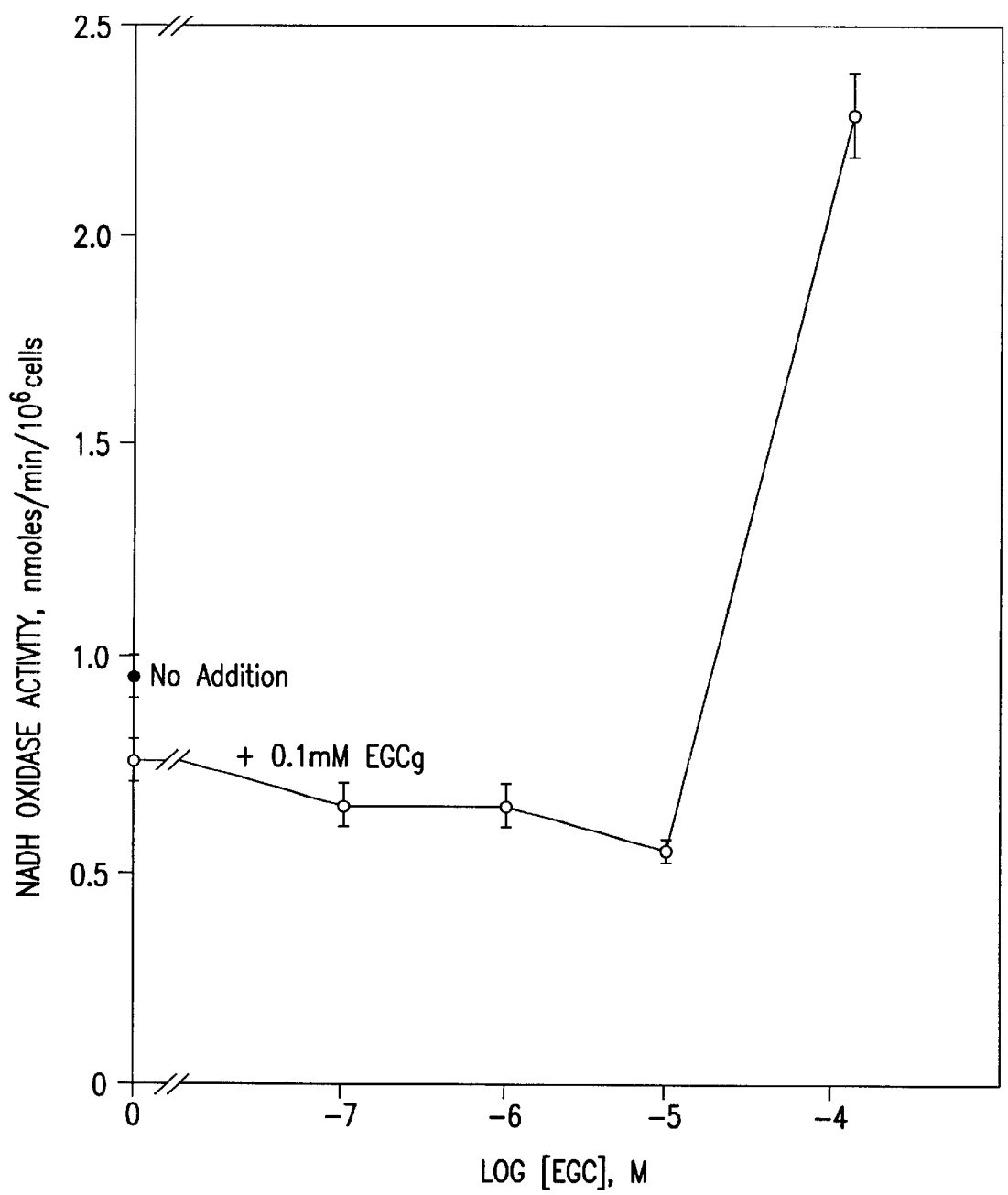

FIG. 15. Response of the NADH oxidase of 4T1 mouse mammary cells to varying concentrations of (-)-epigallocatechin (EGC) in the presence of $10^{-7}$ M (-)-epigallocatechin gallate (EGCg). The tNOX activity was completely inhibited by $10^{-5}$ M EC in the presence of 0.1 mM EGCg without effect on CNOX activity. Values are averages of duplicate determinations from 2 experiments±mean average deviations between the two experiments.

Figure 16:
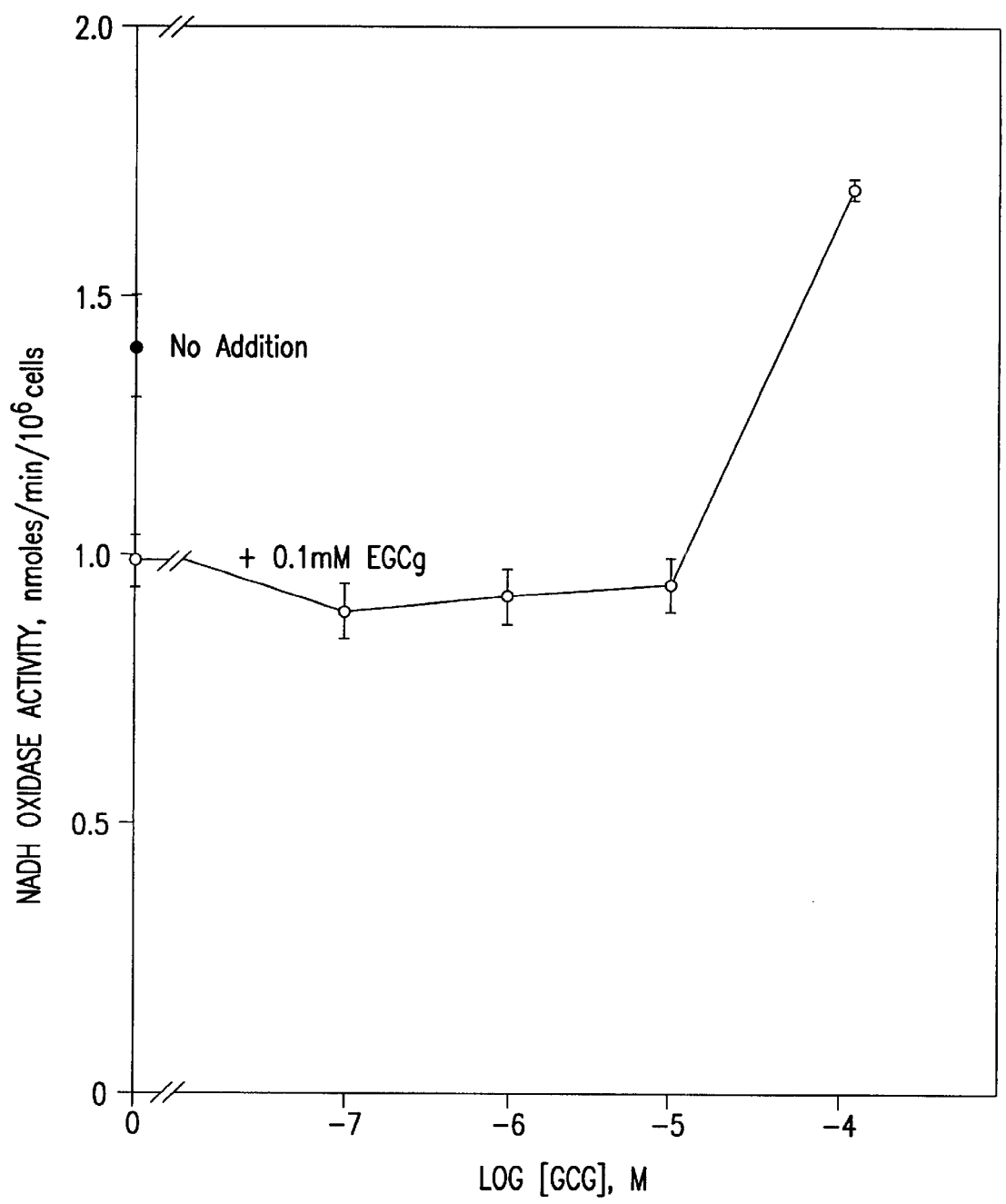

FIG. 16. Response of the NADH oxidase of 4T1 mouse mammary cells to varying concentrations of (-)-epigallocatechin gallate (GCG) in the presence of $10^{-7}$ M (-)-epigallocatechin gallate (EGCg). The NOX activity was less affected by GCG in the presence of 0.1 mM EGCg than for EC (Table 5), ECG (FIG. 14) or EGC (FIG. 15). Values are averages of duplicate determinations from 2 experiments±standard deviations among the three experiments.

Figure 17:
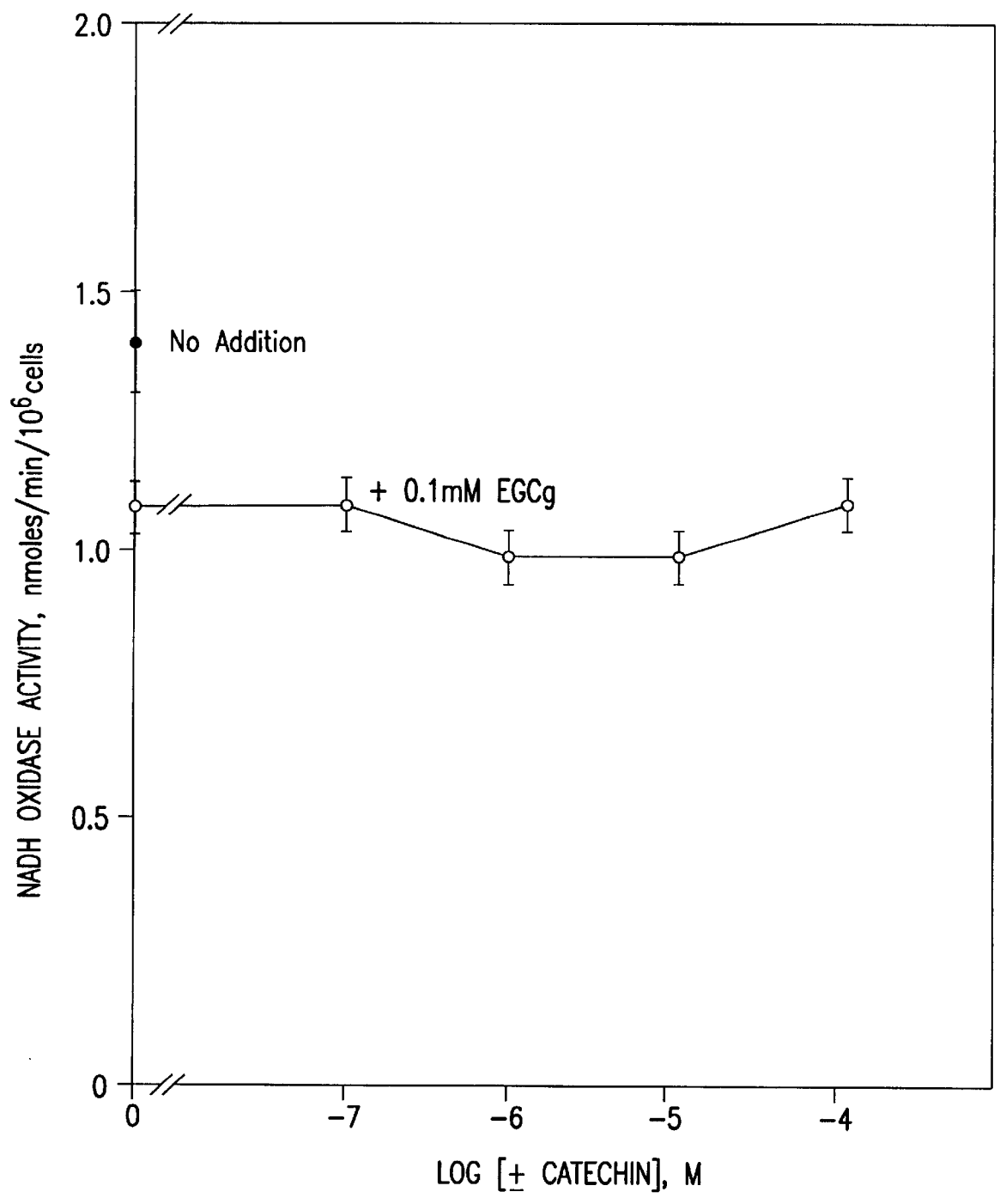

FIG. 17. Response of the NADH oxidase of 4T1 mouse mammary cells to varying concentrations of ±catechin in the presence of $10^{-7}$ M (-)-epigallocatechin gallate (EGCg). The NOX activity was little affected by ±catechin either in the presence or absence (not shown) of 0.1 mM EGCg. Values are averages of duplicate determinations from 3 experiments±standard deviations among the three experiments.

Figure 18:
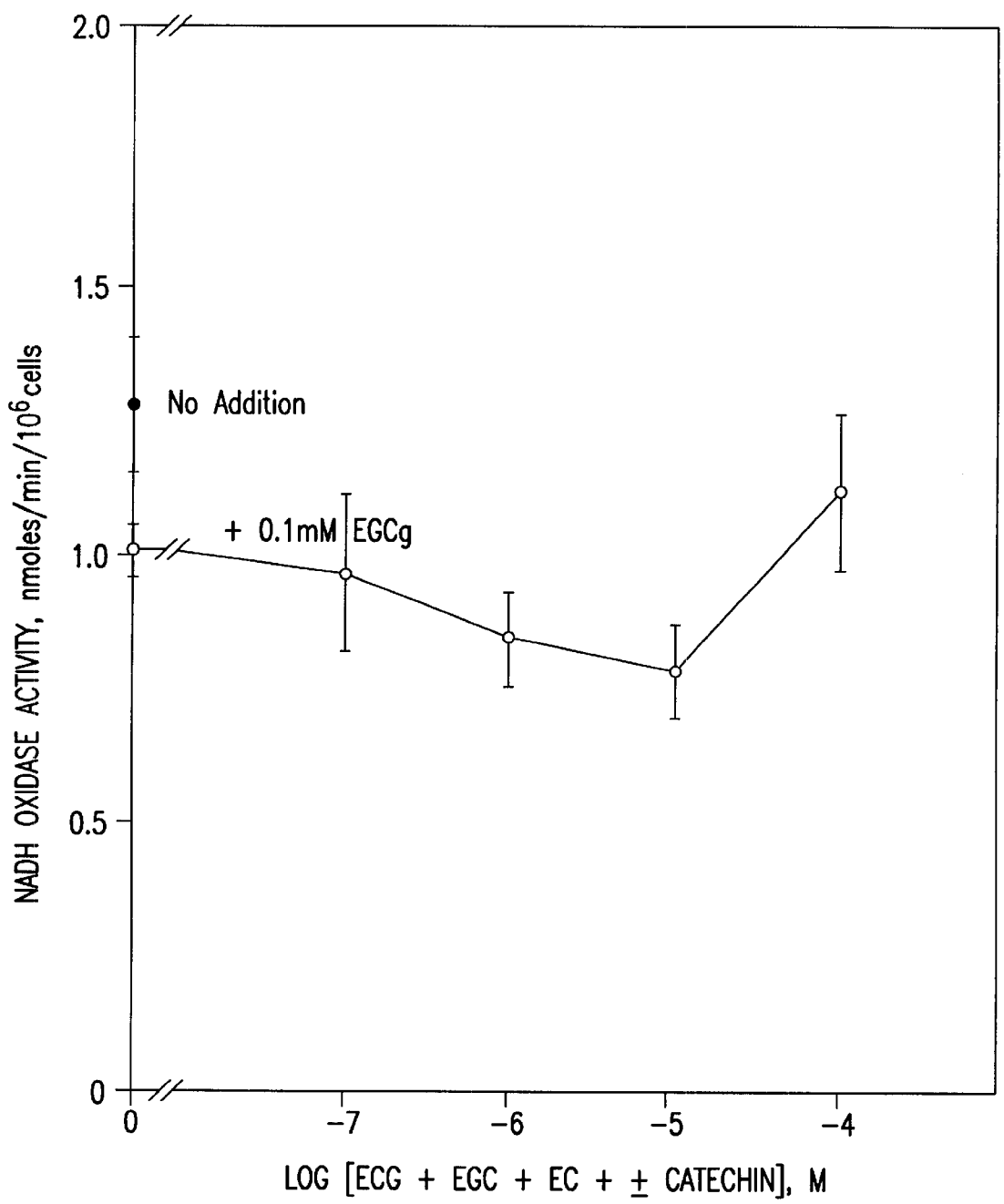

FIG. 18. Response of the NADH oxidase of 4T1 mouse mammary cells to varying concentrations of a mixture of equal parts of ECG, EGC, EC and±catechin in the presence of $10^{-7}$ M (-)-epigallocatechin gallate (EGCg). The NOX activity was completely inhibited by $10^{-5}$ to $10^{-6}$ M of the mixture in the presence of 0.1 mM EGCg without effect on CNOX activity. Values are averages of duplicate determinations from 3 experiments±standard deviations among the three experiments.

Figure 19:
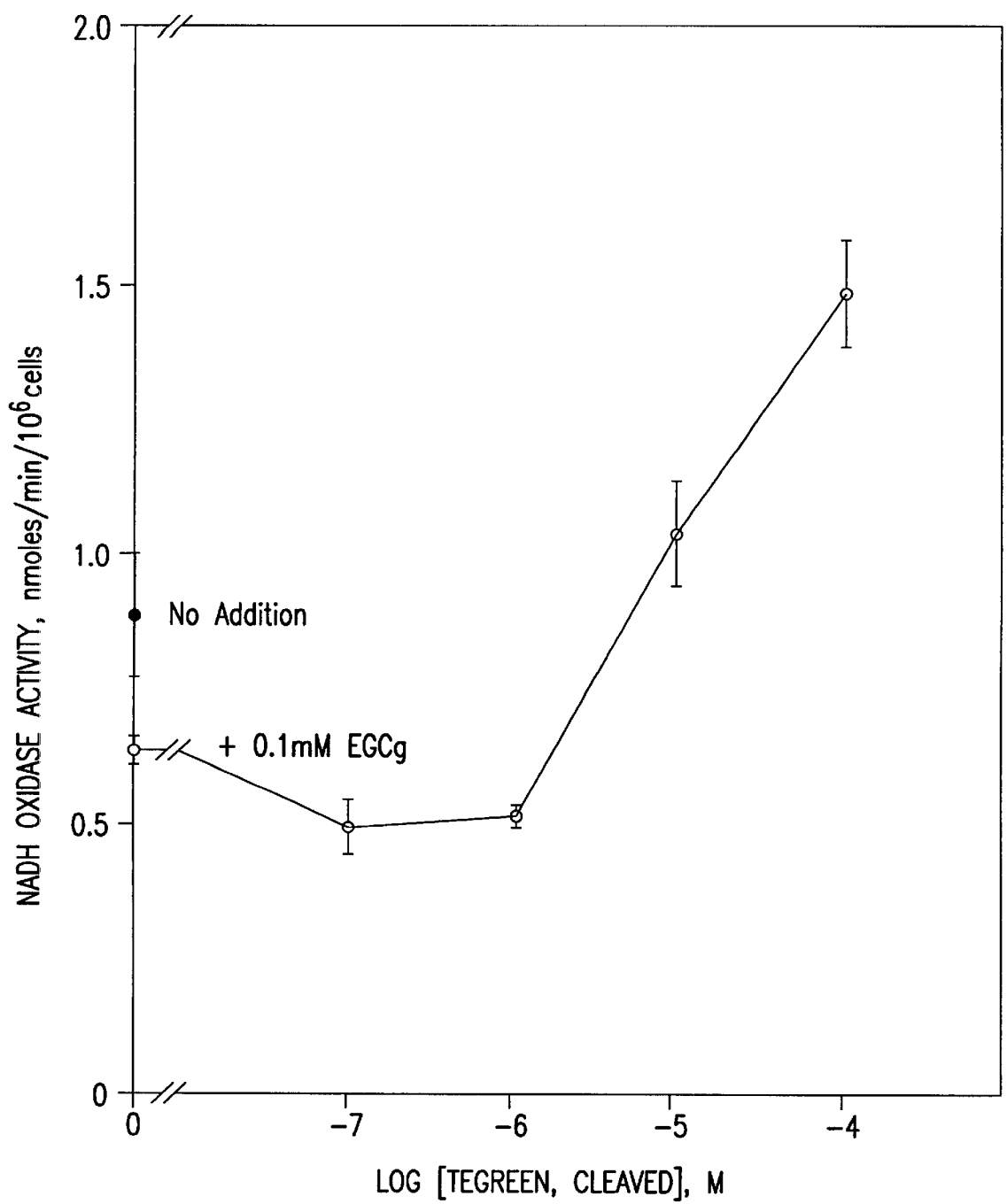

FIG. 19. Response of the NADH oxidase of 4T1 mouse mammary cells to varying concentrations of Tegreen™ a concentration equivalent to $10^{-7}$ EGCg treated with NaOH to cleave gallate esters. The hydrolyzate was tested in the presence of $10^{-7}$ M (-)-epigallocatechin gallate (EGCg). The base was neutralized to pH 7 with HCl and a control experiment with an equivalent amount of NaCl was carried out. The tNOX activity was completely inhibited by EGCg of Tegreen™ in the presence of 0.1 mM EGCg without effect on CNOX activity. Values are averages of duplicate determinations from 2 experiments±mean average deviations between the two experiments.

5. DETAILED DESCRIPTION OF THE INVENTION

The invention described herein encompasses catechin formulations comprising epigallocatechin gallate (EGCg), epicatechin gallate (ECG), epigallocatechin (EGC), and epicatechin (EC) in novel combinations thereof, and optionally in combination with other polyphenols or other anticancer therapeutic agents.

The disclosure is based, in part, on the discovery that surprisingly small levels of (−)-epigallocatechin gallate (EGCg) inhibits the activity of a cancer-specific protein, an isoform of NADH oxidase specific to cancer cells (tNOX). Typically, the amount of EGCg in green tea extract is found to approximate 10–15% of the catechins and is thought to be the major biologically active catechin. Studied on the effects of green tea extract on cells have utilized green tea extract having at least 10–15% EGCg, i.e. the naturally occurring amount, and often as much as 30% EGCg. The inhibition of tNOX results in the inhibition of cell growth, and ultimately, apoptosis of the cancer cell, whereas normal cells (which lack tNOX but instead express the isoform CNOX) are less affected. Thus, the invention provides a potent preventative and therapeutic effect without or while reducing the adverse effects on normal, healthy cells.

In one embodiment, the catechin formulation contains about 0.01% of EGCg of the total catechins. In another embodiment, the catechin formulations contain about 0.1% of EGCg of the total catechins. In yet another embodiment, the catechin formulation contains about 1.0% of EGCg of the total catechins. In yet another embodiment, the catechin formulation contain about 5.0% of EGCg of the total catechins. In another embodiment, the catechin formulation contain less than 10% of EGCg of the total catechins.

In another embodiment, the ratio of EC to EGCg concentration is about 10:1. In another embodiment, the ratio of EC to EGCg concentration is about 100:1. In yet another embodiment, the ratio of EC to EGCg concentration is about 1000:1.

This is based upon the discovery that catechin combinations wherein the level of EGCg is small compared to other catechins, particularly EC is also an effective inhibitor of the activity of tNOX.

In another embodiment of the invention, a method of preparing compositions containing reduced levels of EGCg is disclosed.

In accordance with the present invention, the catechin formulations with reduced levels of EGCg can be used alone or in combination with other known biological agents as dietary supplements or pharmaceuticals in the treatment or prevention of cancer. The catechins can be used before, during, or after the administration of one or more known chemotherapeutic agents, including antitumor agents. In addition, the catechins can be used before, during, or after radiation treatment.

In another embodiment, the compositions of the invention are sterile pharmaceutical compositions suitable for intravenous injection or infusion.

In another embodiment, the invention encompasses a composition suitable for oral delivery, comprising catechins and a pharmaceutically acceptable excipient or carrier. A preferred embodiment comprises a sustained release composition to maintain the circulating levels of said composition at a certain minimum level for therapeutic efficacy over a specified time period. Specific therapeutic regimens, pharmaceutical compositions, and kits are also provided by the invention.

Since novel formulations of catechins are disclosed herein, the invention also encompasses methods of using said novel formulations for the treatment and prevention of cancer in a mammal, wherein the mammal is preferably a human.

Particular compositions of the invention and their uses are described in the sections and subsections which follow.

5.1. Catechin Formulations

The invention comprises formulations (e.g., specific combination of catechins and specific levels) of green tea polyphenols, in particular, catechins, for the treatment and prevention of cancer. The typical percentage of the individual catechins in green tea extracts is 10–15% EGCg, 2–3% ECG, 2% EC, and 2–3% EGC (Suganuma et al., 1999, Can. Res. 59:44–47).

In one embodiment, the catechin formulation contains about 0.01% of EGCg of the total catechins. In another embodiment, the catechin formulations contain about 0.1% of EGCg of the total catechins. In yet another embodiment, the catechin formulation contains about 1.0% of EGCg of the total catechins. In yet another embodiment, the catechin formulation contain about 5.0% of EGCg of the total catechins. In another embodiment, the catechin formulation contain less than 10% of EGCg of the total catechins.

In another embodiment, the ratio of EC to EGCg concentration is about 10:1. In another embodiment, the ratio of EC to EGCg concentration is about 100:1. In yet another embodiment, the ratio of EC to EGCg concentration is about 1000:1.

Based upon results, maintaining or dosing EGCg levels over a certain period of time is preferred. In a preferred embodiment, the invention includes a unique feature of administration comprising a sustained release formulation so a constant level of EGCg is maintained between $10^{-8}$ and $10^{-6}$ M between 48 to 96 hours in the sera. Such sustained and/or timed release formulations may be made by sustained release means or delivery devices that are well known to those of ordinary skill in the art, such as those described in U.S. Pat. Nos.: 3,845,770, 3,916,899, 3,536,809, 3,598,123, 4,008,719, 4,710,384, 5,674,533, 5,059,595, 5,591,767, 5,120,548, 5,073,543, 5,639,476, 5,354,556, and 5,733,566, the disclosures of which are each incorporated herein by reference. These pharmaceutical compositions can be used to provide slow or sustained release of one or more of the active ingredients using, for example, hydropropylmethyl cellulose, other polymer matrices, gels, permeable membranes, osmotic systems, multilayer coatings, microparticles, liposomes, microspheres, or the like, or a combination thereof to provide the desired release profile in varying proportions. Suitable sustained release formulations known to those of ordinary skill in the art, including those described herein, may be readily selected for use with the pharmaceutical compositions of the invention. Thus, single unit dosage forms suitable for oral administration, such as, but not limited to, tablets, capsules, gelcaps, caplets, powders, and the like, that are adapted for sustained release are encompassed by the present invention.

In another preferred embodiment, the sustained release formulation contains active ingredients such as, but not limited to, microcrystalline cellulose, maltodextrine, ethylcellulose, and magnesium stearate. In yet another highly preferred embodiment, the formulation is synthesized with a CapsuDar® SR (Biodar, Yavne, Israel) microencapsulation which consists of the active ingredients microcrystalline cellulose, maltodextrine, ethylcellulose, and magnesium stearate.

The level of caffeine is generally less than about 5% and is preferably less than 0.5% of the catechins.

The invention comprises all pharmaceutically acceptable derivatives of the catechins listed supra, and their combinations thereof.

5.2. Preparation of Formulations with Reduced EGCg

The invention further comprises a method of preparing combinations of catechins which have reduced levels of EGCg. The method involves the use the enzyme tannase (Tanin acyl hydrolase EC 3.1.1.20), which is produced by various species of Aspergillus and Penicillium, to hydrolyze esters of phenolic acids. Certain tea catechins are esters of a phenolic acid called gallic acid, e.g. EGCg, ECG and GCG (FIG. 1). In alternate terminology, these tea catechins have a gallate moiety. Preferably the tannase is from *Aspergillus oryzae* (Kikkoman Corp., Japan). When incubated with green tea extract, the tannase cleaves the gallate moiety from the rest of the molecule, thus releasing gallic acid. Thus, the incubation of green tea extract with tannase reduces the amount of ECG, EGCg and GCG present and, thus, produces EC, EGC, GC and gallic acid.

The tannase enzyme can have any amount of measurable activity. Preferably, the tannase has an activity of about 500 units/g. One unit of activity is defined as the amount of enzyme which is able to hydrolyze 1 $\mu$mol of phenolic ester bond per minute at 30° C. and at pH 5.5.

The tannase is combined with green tea extract in a buffer solution. The buffer solution may be any buffer that maintains the pH between 5.0 and 7.0. Preferably, the incubation is carried out at pH between 6.0 and 6.4. Most preferably the incubation is carried out at pH 6.2. Example of a buffer solution is 0.2 M $NaH_2PO_4$ combined with 0.005 M $K_2HPO_4$ and $Na_2HPO_4$ combined with $NaH_2PO_4$ to form a 0.02 M solution. The amount of buffer solution in which the incubation takes place is not critical.

The tannase is allowed to incubate with the green tea extract until the reaction is completed, meaning that the desired amounts of ECG, EGCg and GCG have been converted to EC, EGC and GC, respectively. In one example, the incubation step is allowed to run for 30 minutes at 40° C.

Alternately, the incubation step can be carried out by immobilizing the tannase on a resin. Any anion exchange resin is a suitable substrate on which to immobilize the tannase. Preferably a macroporous polystyrene resin is used. The tannase may be directly or indirectly attached to the resin. If the tannase is indirectly attached to the resin then a linker molecule will connect the tannase to the resin. A suitable linker is glutaraldehyde. Whether the attachment is direct or indirect, the tannase is preferably covalently bonded to the resin or the linker, respectively.

To prepare the immobilized tannase, the resin is wetted with a suitable buffer, such as described above, with a pH of about 6.8, and combined with a solution of the linker molecule in the same buffer. The resin-linker solution should be stirred for a time sufficient to bond the linker to the resin. Preferably the reaction is allowed to continue for about 2 hours. The buffer is decanted and the modified resin is washed with water to remove unbound linker. The enzyme is dissolved in the buffer at a pH of 6.8 and the modified resin is added to the enzyme-buffer solution. The resin-enzyme solution is then stirred at room temperature for a time sufficient to bond the enzyme to the modified resin. Preferably the reaction is allowed to continue for up to 15 hours. Excess tannase is removed with washes of buffer. If need be, the activated resin with immobilized tannase can be stored in buffer, preferably with pH in the range of 6.4–6.8.

The activated resin exhibits the best results at pH of 6.0–7.0 with reaction temperatures up to 50° C. The activated resin can be placed in conventional liquid chromatography apparatus. For example, a separation column or a packed-bed reactor which allows continuously flowing reactions can be considered suitable apparatus. Green tea extract in buffer is then eluted through the activated resin with the buffer used as a effluent. Preferably the elution is carried out at pH 6.8. The efficiency with which the immobilized tannase hydrolyzes the phenolic ester bonds of the green tea extract depends on the flow rate of the effluent. A flow rate of 1 ml/min being preferred and a rate of 0.1 ml/min being most preferred.

After the incubation step, the water in the reaction mixture may be evaporated to produce a reddish-brown extract. Alternately, the reaction mixture may be extracted with an organic solvent. After extraction, the organic solvent phase is separated from the aqueous phase. This extraction step may be carried out repeatedly, with each new extraction utilizing fresh organic solvent. The organic solvent is preferably a halogenated solvent or ethyl acetate. The organic solvent extracts are combined and the organic solvent is evaporated to produce a dry residue.

Optionally, the dried residue may be further processed using liquid chromatography to remove impurities. The dried residue is dissolved in a solvent and applied to a separation column. The column is eluted with the same solvent. The solvent is preferably 90% ethanol. Fractions from the column are collected and analyzed using thin layer chromatography (TLC). Fractions containing the desired products are combined and evaporated to dryness. Preferably gallic acid is one of the impurities removed through the use of the liquid chromatography step.

Optionally, EGCg may be added back to the formulation obtained by the presented method to precisely obtain the desired percentages or ratios of EGCg to other catechins.

This method of reducing the level of EGCg may be practiced on any scale, from bench top scale to pilot plant scale to full scale production scale. Stated another way, this method can be utilized to produce milligrams, kilograms or tons of novel catechin formulations where the level of EGCg is reduced.

5.3. Target Cancers

Cancers that can be treated by the methods of the present invention include, but not limited to human sarcomas and carcinomas, e.g., fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, meningioma, melanoma, neuroblastoma, retinoblastoma; leukemias, e.g., acute lymphocytic leukemia and acute myelocytic leukemia (myeloblastic, promyelocytic, myelomonocytic, monocytic and erythroleukemia); chronic leukemia (chronic myelocytic (granulocytic) leukemia and chronic lymphocytic leukemia); and polycythemia vera, lymphoma (Hodgkin's disease and non-Hodgkin's disease), multiple myeloma, Waldenström's macroglobulinemia, and heavy chain disease.

In a preferred embodiment, the cancer is one where circulating levels of tNOX are present in the sera of patients suffering from said cancer, e.g., rectal carcinoma, colon carcinoma, breast carcinoma, ovarian carcinoma, small cell lung carcinoma, colon carcinoma, chronic lymphocytic carcinoma, hairy cell leukemia, osophogeal carcinoma, prostate carcinoma, breast cancer, myeloma, and lymphoma, see e.g., U.S. Pat. No. 5,605,810, which is incorporated by reference in its entirety.

In a preferred embodiment, the patient already has cancer and is undergoing treatment for said cancer. In a specific embodiment, the patient already has cancer but no metastasis. i.e., secondary cancer. In another specific embodiment, the patient already has cancer plus a metastatic cancer. In another specific embodiment, the patient having a cancer is immunosuppressed by reason of having undergone anti-cancer therapy (e.g., chemotherapy or radiation) prior to administration of the catechin complexes of the invention.

In another specific embodiment, the cancer is a tumor. In a preferred embodiment, the tumor is a tumor of epithelial tissue, lymphoid tissue, connective tissue, bone, or central nervous system.

5.4. Combination Therapy

The invention encompasses the catechin formulations listed in Section 5.1 administered in combination with other therapeutic agents, such as anti-cancer drugs. The therapeutic agents include, but are not limited to adriamycin and adriamycin conjugates, mechlorethamine, cyclophosphamide, ifosfamide, melphalan, chlorambucil, hex amethylmelamine, thiotepa, busulfan, carmustine, lomustine, semustine, streptozocin, dacarbazine, methotrexate, fluorouacil, floxuridie, cytarabine, mercaptopurine, thioguanine, pentostatin, vinblastine, vincristine, etoposide, teniposide, actinomycin D, daunorubicin, doxorubicin, bleomycin, plicamycin, mitomycin, L-asparaginase, interferon-alpha, cisplatin, carboplatin, mitoxantrone, hydroxyurea, procarbazine, mitotane, aminoglutethimide,, prednisone, hydroxyprogesterone caproate, medroxyprogesterone acetate, megestrol acetate, diethylstilbestrol, ethinyl estradiol, tamoxifen, testosterone propionate, fluoxymesterone, flutamide, leuprolide, acetogenins, e.g., bullatacin, and quassanoids, e.g. simalikalactone D and glaucarubolone, and pharmaceutically acceptable derivatives thereof. The therapeutic agents which inhibit tNOX and cancer cell growth include adriamycin, bullatacin, simalikalactone D, and glaucarubolone has been demonstrated by the Inventors in U.S. Pat. No. 5,605,810, which is incorporated by reference in its entirety for all purposes.

The invention also embodies the catechin formulations, anti-cancer agents, and combinations thereof for the treatment of cancer patients undergoing chemotherapy and/or irradiation for a primary cancer. In a preferred embodiment, the catechin formulations, anti-cancer agents, and combinations thereof provides a method for treating the metastasized, i.e. secondary cancer, in said patients.

In another embodiment, the secondary agent administered, in addition to the catechin formulations, includes a monoclonal antibody directed against tNOX for combination therapy. A monoclonal antibody to the human tNOX protein isolated from the sera of cancer patients has already successfully been used in the expression cloning of tNOX from HeLa cells (Chueh et al., 1997, Arch. Biochem. Biophys. 342:38–44).

5.5. Pharmaceutical Composition and Modes of Administration

Catechin complexes of the invention may be formulated into pharmaceutical preparations for administration to mammals for treatment of cancer. In a preferred embodiment, the mammal is a human.

Compositions comprising a compound of the invention formulated in a compatible pharmaceutical carrier may be prepared, packaged, and labeled for treatment of the indicated cancer, such as human sarcomas and carcinomas, e.g., fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, meningioma, melanoma, neuroblastoma, retinoblastoma; leukemias, e.g., acute lymphocytic leukemia and acute myelocytic leukemia (myeloblastic, promyelocytic, myelomonocytic, monocytic and erythroleukemia); chronic leukemia (chronic myelocytic (granulocytic) leukemia and chronic lymphocytic leukemia); and polycythemia vera, lymphoma (Hodgkin's disease and non-Hodgkin's disease), multiple myeloma, Waldenström's macroglobulinemia, and heavy chain disease.

If the complex is water-soluble, then it may be formulated in an appropriate buffer, for example, phosphate buffered saline or other physiologically compatible solutions. Alternatively, if the resulting complex has poor solubility in aqueous solvents, then it may be formulated with a non-ionic surfactant such as Tween, or polyethylene glycol. Thus, the compounds and their physiologically acceptable solvates may be formulated for administration by inhalation or insufflation (either through the mouth or the nose) or oral, buccal, parenteral, rectal administration or, in the case of tumors, directly injected into a solid tumor.

For oral administration, the pharmaceutical preparation may be in liquid form, for example, solutions, syrups or suspensions, or may be presented as a drug product for reconstitution with water or other suitable vehicle before use. Such liquid preparations may be prepared by conventional means with pharmaceutically acceptable additives such as suspending agents (e.g., sorbitol syrup, cellulose derivatives or hydrogenated edible fats); emulsifying agents (e.g., lecithin or acacia); non-aqueous vehicles (e.g., almond oil, oily esters, or fractionated vegetable oils); and preservatives (e.g., methyl or propyl-p-hydroxybenzoates or sorbic acid). The pharmaceutical compositions may take the form of, for example, tablets or capsules prepared by conventional means with pharmaceutically acceptable excipients such as binding agents (e.g., pregelatinized maize starch, polyvinyl pyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycolate); or wetting agents (e.g., sodium lauryl sulphate). The tablets may be coated by methods well-known in the art. In a preferred embodiment, the pharmaceutical composition may take the form of a capsule or powder to be dissolved in a liquid for oral consumption.

Preparations for oral administration may be suitably formulated to give controlled release of the active compound.

For buccal administration, the compositions may take the form of tablets or lozenges formulated in conventional manner.

The compounds may be formulated for parenteral administration by injection, e.g., by bolus injection or continuous infusion. Formulations for injection may be presented in unit dosage form, e.g., in ampules or in multi-dose containers, with an added preservative. The compositions may take such forms as suspensions, solutions or emulsions in oily or aqueous vehicles, and may contain formulatory agents such as suspending, stabilizing and/or dispersing agents. Alternatively, the active ingredient may be in powder form for constitution with a suitable vehicle, e.g., sterile pyrogen-free water, before use.

The compounds may also be formulated in rectal compositions such as suppositories or retention enemas, e.g., containing conventional suppository bases such as cocoa butter or other glycerides.

In addition to the formulations described previously, the compounds may also be a formulated as a sustained and/or timed release formulation. Response to the subject compounds is reversible (see Example 6, infra) and the levels of circulating catechin compositions must be maintained above some minimum therapeutic dose to kill cancer cells. Such sustained and/or timed release formulations may be administered by implantation (for example, subcutaneously or intramuscularly) or by intramuscular injection. Thus, for example, the compounds may be formulated with suitable polymeric or hydrophobic materials (for example, as an emulsion in an acceptable oil) or ion exchange resins, or as sparingly soluble derivatives, for example, as a sparingly soluble salt. Liposomes and emulsions are well known examples of delivery vehicles or carriers for hydrophilic drugs. Common timed and/or controlled release delivery systems include, but are not be restricted to, starches, osmotic pumps, or gelatin micro capsules.

The compositions may, if desired, be presented in a pack or dispenser device which may contain one or more unit dosage forms containing the active ingredient. The pack may for example comprise metal or plastic foil, such as a blister pack. The pack or dispenser device may be accompanied by instructions for administration.

The invention also provides kits for carrying out the therapeutic regimens of the invention. Such kits comprise in one or more containers having therapeutically or prophylactically effective amounts of the catechin complexes in pharmaceutically acceptable form. The catechin complex in a vial of a kit of the invention may be in the form of a pharmaceutically acceptable solution, e.g., in combination with sterile saline, dextrose solution, or buffered solution, or other pharmaceutically acceptable sterile fluid. Alternatively, the complex may be lyophilized or desiccated; in this instance, the kit optionally further comprises in a container a pharmaceutically acceptable solution (e.g., saline, dextrose solution, etc.), preferably sterile, to reconstitute the complex to form a solution for injection purposes.

In another embodiment, a kit of the invention further comprises a needle or syringe, preferably packaged in sterile form, for injecting the complex, and/or a packaged alcohol pad. Instructions are optionally included for administration of catechin complexes by a clinician or by the patient.

5.6. Dosage 5.6.1 Catechin Formulations as Dietary Supplements for Preventing Cancer In one embodiment of this invention, a catechin formulation with reduced levels of EGCg may be used as a dietary or nutritional supplement for the prevention of cancer. In this embodiment, the total daily dose ranges of the active catechins for the conditions described herein are generally from about 10 mg to about 800 mg administered in divided doses administered parenterally or orally or topically. A preferred total daily dose is from about 200 mg to about 600 mg of the active catechins.

In a another embodiment, the total daily dose of a catechin formulation with reduced levels of EGCg may be used as a dietary supplement is about 10 mg to about 800 mg of active catechins administered twice daily (e.g., in the morning and the evening) at a dose of about 50 mg to about 400 mg. The dosage forms and compositions may comprise any of the forms and compositions described supra. In a preferred embodiment, the sustained release formulation comprising catechins is a tablet, capsule, gel, or a liquid-soluble powder.

The dietary supplement compositions of the present invention comprise catechins as the active ingredients, as well as ingestable salts thereof, and may also contain an ingestable carrier, and optionally, therapeutic ingredients. The term "ingestable salts" refers to salts prepared from non-toxic acids and bases, including inorganic and organic acids and bases.

The dietary supplement compositions include compositions suitable for oral and parenteral (including subcutaneous, intramuscular, intrathecal, intravenous, and other injectables) routes, although the most suitable route in any given case will depend on the nature and severity of the condition being treated.

In addition, the catechin carrier could be delivered via charged and uncharged matrices used as drug delivery devices such as cellulose acetate membranes, also through targeted delivery systems such as fusogenic liposomes attached to antibodies or specific antigens.

5.6.2 Catechin Formulations as Pharmaceuticals for Treating Cancer

The magnitude of a therapeutic dose of catechin formulations in the acute or chronic management of cancer will vary with the severity of the condition to be treated and the route of administration. The dose, and dose frequency, will also vary according to the age, body weight, condition and response of the individual patient, and the particular catechin formulation used. All formulations described in the specification are encompassed as therapeutic catechin mixtures and it is understood that one of skill in the art would be able to determine a proper dosage of particular catechin formulations using the parameters provided in the invention. In general, the total daily dose ranges of the catechin formulations for the conditions described herein are generally from about 10 mg to about 1000 mg administered in divided doses administered parenterally or orally or topically. A preferred total daily dose is from about 200 mg to about 600 mg of the catechin formulations.

For example, in one embodiment, the daily dose ranges of EGCg and other catechins for the conditions described herein are generally from about 0.2 to about 60 mg per kg body weight of EGCg and about 200 to about 600 mg per kg weight of body of other catechins. Preferably the catechin formulation of the invention is given daily until remission, followed by two to ten additional cycles, each lasting about 60 days in duration. When the dose is administered orally, a sustained release formulation is preferred so that a fairly constant level of catechins is provided over the course of treatment, which is generally at least 48 hours and preferably at least 96 hours per cycle. As the catechins are not particularly toxic, the formulation may be administered for as long as necessary to achieve the desired therapeutic effect.

In the case where an intravenous injection or infusion composition is employed, a suitable dosage range for use is, e.g., from about 0.6 to about 60 mg per kg body weight of EGCg and about 6 to about 600 mg per kg body weight of other catechins total daily.

For treatment of solid tumors, a preferred dosing regimen involves intravenous infusion of about 6 to about 120 mg per kg body weight of EGCg and about 60 to about 600 mg per kg body weight of other catechins per day. This daily treatment protocol is repeated once per month until the tumor growth tumor is inhibited or when the tumor shows signs of regression.

In one preferred embodiment, EGCg is 0.01% of the total catechins in the formulation. So, in one non-limiting example, 200 to 600 mg of the total formulation will be required for a dose of 0.02 to 0.06 mg of EGCg.

In another preferred embodiment, EGCg is 0.1% of the total catechins. So, in this non-limiting example, 200 to 600 mg of the total formulation will be required for a dose of 0.2 to 0.6 mg of EGCg.

In another preferred embodiment, EGCg is 1.0% of the total catechins. So, in this non-limiting example, 200 to 600 mg of the total formulation will be required for a dose of 2 to 6 mg of EGCg.

For example, in one embodiment, the daily dose ranges of EGCg and EC for the conditions described herein are generally from about 0.2 to about 60 mg per kg body weight of EGCg and 200 to about 600 mg per kg weight of body EC. Preferably the catechin formulation of the invention is given daily until remission, followed by two to ten additional cycles, each lasting about 60 days in duration. When the dose is administered orally, a sustained release formulation is preferred so that a fairly constant level of catechins is provided over the course of treatment, which is generally at least 48 hours and preferably at least 96 hours per cycle. As the catechins are not particularly toxic, the formulation may be administered for as long as necessary to achieve the desired therapeutic effect.

In the case where an intravenous injection or infusion composition is employed, a suitable dosage range for use is, e.g., from about 0.6 to about 60 mg per kg body weight of EGCg and about 6 to about 600 mg per kg body weight of EC total daily.

For treatment of solid tumors, a preferred dosing regimen involves intravenous infusion of about 6 to about 120 mg per kg body weight of EGCg and about 60 to about 600 mg per kg body weight of EC per day. This daily treatment protocol is repeated once per month until the tumor growth tumor is inhibited or when the tumor shows signs of regression.

In one preferred embodiment, the ratio of EC to EGCg is about 1000:1. So, in one non-limiting example, 200 to 600 mg of EC will be required for a dose of 0.2 to 0.6 mg of EGCg.

In another preferred embodiment, the ratio of EC to EGCg is about 100:1. So, in this non-limiting example, 200 to 600 mg of EC will be required for a dose of 2 to 6 mg of EGCg.

In another preferred embodiment, the ratio of EC to EGCg is about 10:1. So, in this non-limiting example, 200 to 600 mg of EC will be required for a dose of 20 to 60 mg of EGCg.

In an alternative embodiment of the invention, the effect of the therapy with catechin formulations having reduced levels of EGCg on cancer treatment can be monitored by any methods known in the art, including but not limited to monitoring circulating tNOX activity in patient sera, as well as more traditional approaches such as determining levels of tumor specific antigens and putative biomarkers, e.g., carcinoembryonic antigens (CEA), alpha-fetoprotein; and changes in morphology and/or size using computed tomographic scan and/or sonogram.

Desirable blood levels may be maintained by a continuous infusion of catechin formulations having reduced levels of EGCg as ascertained by plasma levels. It should be noted that the attending physician would also know how to and when to adjust treatment to higher levels if the clinical response is not adequate (precluding toxic side effects, if any).

Again, any suitable route of administration may be employed for providing the patient with an effective dosage of catechin formulations having reduced levels of EGCg of this invention. Dosage forms include tablets, troches, cachet, dispersions, suspensions, solutions, capsules, gel caps, caplets, compressed tablets, sustained release devices, patches, and the like.

The pharmaceutical compositions of the present invention comprise catechins as the active ingredients, as well as pharmaceutically acceptable salts thereof, and may also contain a pharmaceutically acceptable carrier, and optionally, other therapeutic ingredients. The term "pharmaceutically acceptable salts" refers to salts prepared from pharmaceutically acceptable non-toxic acids and bases, including inorganic and organic acids and bases.

The pharmaceutical compositions include compositions suitable for oral and parenteral (including subcutaneous, intramuscular, intrathecal, intravenous, and other injectables) routes, although the most suitable route in any given case will depend on the nature and severity of the condition being treated.

In addition, the catechin carrier could be delivered via charged and uncharged matrices used as drug delivery devices such as cellulose acetate membranes, also through targeted delivery systems such as fusogenic liposomes attached to antibodies or specific antigens.

In practical use, catechins can be combined as the active ingredient(s) in intimate admixture with a pharmaceutical carrier according to conventional pharmaceutical compounding techniques. The carrier may take a wide variety of forms depending on the form of preparation desired for administration, e.g., oral or parenteral (including tablets, capsules, powders, intravenous injections or infusions). In preparing the compositions for oral dosage form any of the usual pharmaceutical media may be employed, e.g., water, glycols, oils, alcohols, flavoring agents, preservatives, coloring agents, and the like; in the case of oral liquid preparations, e.g., suspensions, solutions, elixirs, liposomes and aerosols; starches, sugars, micro-crystalline cellulose, diluents, granulating agents, lubricants, binders, disintegrating agents, and the like in the case of oral solid preparations e.g., powders, capsules, and tablets. In preparing the compositions for parenteral dosage form, such as intravenous injection or infusion, similar pharmaceutical media may be employed, e.g., water, glycols, oils, buffers, sugar, preservatives and the like know to those skilled in the art. Examples of such parenteral compositions include, but are not limited to Dextrose 5% (w/v), normal saline or other solutions. The total dose of the catechins may be administered in a vial of intravenous fluid, e.g., ranging from about 0.01 to about 1000 mg per kg body weight of catechins. The volume of dilution fluid will vary according to the total dose administered and over the length of the period of time of administration.

An exemplary course of treatment of a patient with cancer or solid cancer can involve daily administration by intravenous infusion of catechins in an aqueous solution at a daily dose of about 6 to about 120 mg of the EGCg and about 60 to about 600 mg of other catechins compositions per kg of body weight of the patient. The course of treatment may be repeated for up to ten times over approximately 10 months with a break of about three to six weeks in between courses. The post-remission course of treatment involves infusion of EGCg and other catechins at a daily dose of about 200 to about 600 mg per kg of body weight of the patient on a daily or weekdays-only basis for a cumulative total of 25 days.

Another exemplary course of treatment of a patient with cancer or solid cancer can involve daily administration by intravenous infusion of catechins in an aqueous solution at a daily dose of about 6 to about 120 mg of the EGCg and about 60 to about 600 mg of EC per kg of body weight of the patient. The course of treatment may be repeated for up to ten times over approximately 10 months with a break of about three to six weeks in between courses. The post-remission course of treatment involves infusion of EGCg and EC at a daily dose of about 200 to about 600 mg per kg of body weight of the patient on a daily or weekdays-only basis for a cumulative total of 25 days.

For the purposes described above, the invention also encompasses methods for monitoring patient response to tea catechins. By monitoring circulating tNOX activity in patient sera, it will be possible to determine therapeutic dosages and to monitor therapeutic benefit from tea catechins. The response of neoplastic cells to the subject compositions may be monitored by assaying the blood or urine of the patient for the NOX activity that is responsive to the catechin compositions, i.e., tNOX. Various assays may be used to monitor activity, such as a NOX assay for neoplasia determination see e.g., U.S. Pat. No. 5,605,810, which is incorporated by reference in its entirety. By following the above monitoring procedures, an effective dosage of the subject compositions may be administered in accordance with the requirement of an individual patient.

6. EXAMPLE

Epigallocatechin Gallate Inhibits Preferentially the NADH Oxidase and Growth of Transformed Cells in Culture 6.1. Materials and Methods 6.1.1. Growth of Cells HeLa (ATCC CCL2) cells were grown in 175 cm$^2$ flasks in Minimal Essential Medium (Gibco), pH 7.4, at 37° C. with 10% bovine calf serum (heat-inactivated), plus 50 mg/l gentamycin sulfate (Sigma). Cells were harvested by scraping and taken up in 140 mM NaCl, 5 mM KCl, 0.7 mM Na$_2$HPO$_4$ and 25 mM Tris, pH 7.4 to a final cell concentration of 0.1 g wet weight (gww) per ml.

MCF-10A human mammary epithelial cells were cultured in a 1:1 mixture of Ham's F12 medium and Dulbecco's Modified Eagle's medium containing cholera enterotoxin (100 ng/ml), insulin (10 μg/ml), hydrocortisone (0.5 gg/ml), epidermal growth factor (EGF, 20 mg/ml), and 5% horse serum. Media were renewed every 2–3 days.

BT-20 human breast adenocarcinoma cells were cultured in Eagle's minimal essential medium nonessential amino acids and Earle's balanced salts supplement with 10% fetal bovine serum. Media were renewed as for MCF-10A cells.

Cell lines were from the American Type Culture Collection (Rockville, Md.).

6.1.2. Purification of Plasma Membranes from Cultured Cells

Cultured cells were collected by centrifugation for 6–15 min at 175–1000×g. The cell pellets were resuspended in 0.2 mM EDTA in 1 mM NaHCO$_3$ in an approximate ratio of 1 ml per 10$^8$ cells and incubated on ice for 10–30 min to swell the cells. Homogenization was achieved in 7- to 8-ml aliquots with a Polytron homogenizer (Brinkmann) for 30–40 sec at 10,500 rpm, using a PT-PA 3012/23 or ST-10 probe. To estimate breakage, the cells were monitored by light microscopy before and after homogenization. At least 90% cell breakage without breakage of nuclei was achieved routinely.

The homogenates were centrifuged for 10 min at 175×g to remove unbroken cells and nuclei and the supernatant was centrifuged a second time at 1.4×10$^6$ g min (e.g., 1 h at 23,500×g) to prepare a plasma membrane-enriched microsome fraction. The supernatant was discarded and the pellets were resuspended in 0.2 M potassium phosphate buffer in a ratio of ~1 ml per pellet from 5×10$^8$ cells. The resuspended membranes were then loaded onto the two-phase system constituted on a weight basis consisting of 6.6% (w/w) Dextran T-500 (Pharmacia) and 6.6% (w/w) Polyethylene Glycol 3350 (Fisher) in a 5 mM potassium phosphate buffer (pH 7.2) for aqueous two-phase separation as described (Morré1971, Methods Enzymol. 22:130–148, and Morré. and Morré, 1989, BioTechniques 7:946–958). The upper phase, enriched in plasma membranes, was diluted 5-fold with 1 mM sodium bicarbonate and the membranes were collected by centrifugation. The purity of the plasma membrane was determined to be >90% by electron microscope morphometry. The yield was 20 mg plasma membrane protein from 10$^{10}$ cells.

6.1.3. Preparation of HeLa Cells and Cell-free Extracts

HeLa S cells were collected by centrifugation and shipped frozen in 0.1 M sodium acetate, pH 5 in a ratio of 1 ml packed cell volume to 1 ml of acetate (Cellex Biosciences, Minneapolis, Minn.). The cells were thawed at room temperature, resuspended and incubated at 37° C. for 1 h to release the protein (del Castillo-Oliveras et al., 1998, Arch. Biochem. Biophys. 358:125–140). The cells were removed by centrifugation at 37,000 g for 60 min and the cell-free supernatants were refrozen and stored in 1 ml aliquots at −70° C.

For heat treatment, 1 ml aliquots of the above supernatant material were thawed at room temperature and heated to 50° C. for 10 min. The denatured proteins were removed by centrifugation (1,500 g, 5 min). Full activity was retained from this step (del Castillo-Oliveras et al., 1998, Arch. Biochem. Biophys. 358:125–140).

For protease treatment, the pH of the heat-stable supernatant was adjusted to 7.8 by addition of 0.1 M sodium hydroxide. *Tritirachium album* proteinase K (Calbiochem) was added (4 ng/ml) and incubated at 37° C. for 1 h with full retention of enzymatic activity and drug response (del Castillo-Oliveras et al., 1998, Arch. Biochem. Biophys. 358:125–140). The reaction was stopped either by freezing for determination of enzymatic activity or by addition of 0.1 M phenylmethylsulfonyl fluoride (PMSF) in ethanol to yield a final concentration of 10 mM PMSF.

6.1.4. Spectrophotometric Assay of NADH Oxidase

NADH oxidase activity was determined as the disappearance of NADH measured at 340 nm in a reaction mixture containing 25 mM Tris-Mes buffer (pH 7.2), 1 mM KCN to inhibit low levels of mitochondrial oxidase activity, and 150 mM NADH at 37° C. with stirring. Activity was measured using a Hitachi U3210 or SLM Aminco DW2000 spectrophotometer with continuous recording over two intervals of 5 min each. A millimolar extinction coefficient of 6.22 was used to determine specific activity. EGCg was added at the final concentrations indicated at the beginning of the assay and was present during the assay period.

Proteins were estimated by the bicinchonic acid method (Smith et al., 1985, Anal. Biochem. 150:76–85) with bovine serum albumin as standard.

6.1.5. Fluorescence Microscopy

Cells were grown for 72 h on glass coverslips placed in small culture dishes with media containing 100 $\mu$M EGCg in ethanol or an equivalent amount of ethanol alone. The coverslips were rinsed and the cells fixed in methanol followed by addition of fluorescent dye 4',6-diamidino-2-phenylindole (DAPI) as described (Wolvetang et al., 1994, FEBS Lett. 339:40–44). Cells were observed and photographed at a primary magnification of 400×.

6.1.6. Determination of EGCg

EGCg was determined with the hot water extracts using the standardized chromatographic procedure described by Katiyar et al. (Katiyar et al., 1992, Nutr. Can. 18:73–83). Authentic EGCg (Sigma) was used as the standard.

6.1.7. Chemicals

All chemicals were from Sigma (St. Louis, Mo.) unless otherwise specified. EGF was from mouse, culture grade, from Upstate Biotechnology Inc. (Lake Placid, N.Y.). Tea infusions were prepared by sequential steeping of ca. 2-g bags of tea (Lipton) in 10 ml of water for 10 min each. At the end of the infusion, bags were pressed to remove liquid.

6.2 Results

6.2.1. NADH Oxidase Activity in Plasma Membrane Vesicles

Epigallocatechin gallate (EGCg) was without effect on the NADH oxidase activity of plasma membrane vesicles (FIG. 2) or NADH oxidase solubilized and partially purified from the cell surface (FIG. 3) of human mammary epithelia (MCF-10A). However, with plasma membranes from human mammary adenocarcinoma (BT-20) or HeLa (human cervical carcinoma) cells, NADH oxidase activities were inhibited by 30 to 40% with an $ED_{50}$ of about 1 nM (FIG. 2). BT-20 and HeLa cells contain a drug-responsive component of NADH oxidase activity inhibited by capsaicin or the antitumor sulfonylurea as well as NADH oxidase activities resistant to inhibition. The responses to EGCg were comparable to those for capsaicin and the sulfonylurea.

With plasma membrane vesicles from the BT-20 mammary adenocarcinoma cell line, the NADH oxidase specific activity was approximately 1.5 that of the MCF-10A cell line (FIG. 2A). Upon addition of EGCg, the specific activity of the MCF-10A cells was unchanged, whereas, that of the BT-20 was reduced to approximately the same level as that of the MCF-10A cells (FIG. 2A). Also inhibited by EGCg in a similar fashion was the NADH oxidase activity from plasma membranes of HeLa cells (FIG. 2B). Thus, in the plasma membrane vesicles from the BT-20 and HeLa cells, there were both EGCg-resistant and EGCg-susceptible components whereas in the plasma membrane vesicles from the MCF 10A cells only an EGCg-resistant activity was observed (FIG. 2A).

6.2.2. NADH Oxidase Activity Released from Cultured Cells

Results similar to those observed with isolated plasma membrane vesicles were obtained as well with solubilized NADH oxidase preparations of NADH oxidase released from cultured cells by low pH treatment (FIG. 3). With BT-20 (FIG. 3A) and HeLa (FIG. 3B) preparations, activity was strongly inhibited by EGCg with an $EC_{50}$ of between 1 and 10 nM. The released and solubilized NADH oxidase for the MCF-10A cells was much less affected by the EGCg (FIG. 3A). As with isolated plasma membrane vesicles, the specific activity of the released NADH oxidase preparations from BT-20 cells was greater (approximately twice) than that of the released preparations from MCF-10A cells. Following treatment with EGCg, the specific activity of the preparations from BT-20 cells was reduced to a level comparable to the specific activity of the preparations from MCF-10A cells. Thus, the EGCg appears to inhibit specifically the drug-responsive NADH oxidase component of the tumorigenically transformed cell lines but not that of the constitutive NADH oxidase activity of the MCF-10A mammary epithelial line.

6.2.3. Effect of EGCg on Intact Cells in Culture

EGCg also inhibited the growth of the BT-20 mammary adenocarcinoma and HeLa cells in culture (FIGS. 2C, D). While not as striking as for the inhibition of NADH oxidase, EGCg did preferentially restrict the growth of the HeLa and BT-20 cells compared to MCF-10A (FIGS. 2C, D). Growth of the MCF-10A mammary epithelial cells was unaffected by EGCg except at very high doses of $10^{-4}$ M (FIG. 2C), whereas that of the tumorigenically transformed BT-20 and HeLa cells was 50% inhibited at about $5 \times 10^{-3}$ M (FIG. 2C, D).

Despite early growth inhibition of MCF-10A cells by EGCg, the cells quickly recovered and eventually grew normally (FIG. 4). This is in contrast to HeLa and BT-20 cells where the cells did not recover and died (FIG. 4).

Measurements of the diameters of treated HeLa and BT-20 cells taken directly from printed micrographs revealed that, on average, the cells treated with $5 \times 10^{-6}$ to $5 \times 10^{-5}$ M EGCg exhibited volumes ~50% those of untreated cells. At $10^{-6}$ M EGCg, there was no response of any of the cell lines at 72 h despite the fact that this EGCg concentration inhibited the tNOX activity of isolated plasma membranes. The possibility was considered that the combination of a reversible inhibition and rapid metabolism of EGCg might result in an overall lack of growth inhibition at $10^{-6}$ M EGCg after 3 days. To test this possibility, cells were treated with $10^{-6}$ M EGCg twice daily for 96 h after which time the cells were photographed, measured and counted. Cell diameters were reduced on average by about 25% and cell volume by 50% by the twice daily $10^{-6}$ M EGCg dosage. Cell number also was reduced by about 25% with both HeLa and BT-20 cells by the $10^{-6}$ M EGCg provided twice daily whereas with the non-cancer MCF-10A cells, growth rate and cell diameters were unaffected or slightly increased. When the cells treated with $10^{-5}$ or $5 \times 10^{-5}$ EGCg were stained to reveal DAPI fluorescence, a very large percentage of the treated cells showed nuclear DNA with the condensed and fragmented appearance characteristic of apoptotic cells (FIG. 5).

6.2.4. Green Tea Inhibits NADH Oxidase

Since EGCg is considered as one of the major compounds contributing to the cancer preventative actions attributed to green tea, green tea infusions were examined as well for their ability to inhibit the NADH oxidase (Weisburger, 1997, Can. Lttr. 114:315–317; Chen et al., 1998, Can. Lttr. 129:173–179; Fujiki et al., 1998, Mutation Res.

402:307–310; Liao et al., 1995; Can. Lttr. 96:239–243; Stoner and Mukhtar, 1995, J. Cell. Biochem. 22:169–180; and Ahmad et al., 1997, J. Nat. Can. Inst. 89:1881–1886). Both the solubilized and partially purified NADH oxidase released from cells by low pH treatment (FIG. 6) and the NADH oxidase of sera pooled from cancer patients (Table 1) were inhibited by green tea infusions. Infusions of green tea (Lipton) were approximately ten times more effective than those of black tea (Lipton) and correlated approximately with the content of EGCg with an $EC_{50}$ of $2\times10^{-6}$ M EGCg equivalent to 1 mg/ml.

TABLE 1

Inhibition of tNOX activity by tea infusions and by epigallocatechin gallate (EGCg), the major tea polyphenol (catechin) of green tea, for sera pooled from patients with cancer. The EGCg content was determined as described (Katiyar et al., 1992, Nutr. Can. 18:73–83). Results were repeated 3 to 5 times with different sources and preparations of both black and green tea and with consistent findings.

| Source | $EC_{50}$ | EGCg (mg/ml) |
|---|---|---|
| Black tea (Lipton) | 1:10 to 1:100 | 1 |
| Green tea (Lipton) | 1:1000 | 1 |
| Epigallocatechin gallate (EGCg) | $2 \times 10^{-6}$ M | 1 |

6.2.5. EGCg Inhibits Cancer Cell Growth

Not only did EGCg inhibit the NADH oxidase of plasma membrane vesicles from cancer cells and not that of normal cells, the substance exerted a parallel response on growth. Growth of HeLa cells was almost completely inhibited by EGCg whereas growth of CHO cells and mammary epithelial cells was much less affected by EGCg. With treated HeLa cells, nuclei exhibited patterns of fluorescence characteristic of apoptosis (Smith et al., 1985, Anal. Biochem. 150:76–85). Thus, the cyanide-resistant NADH oxidase of the plasma membrane appears to represent an enzymatic activity whose inhibition by EGCg correlates with an inhibition of growth and subsequent apoptosis in susceptible cancer cell lines.

7. EXAMPLE

Synergistic Effects of (–)-Epigallocatechin Gallate with (–)-Epicatechin on Inhibition of Cell Surface NADH Oxidase (NOX) Activity and Growth of 4T1 Mouse Mammary and Hela Cells in Culture 7.1. Materials and Methods 7.1.1. Chemicals EGCg and EC were purchased from Sigma (St. Louis, Mo.) or purified from leaves of green tea and supplied by Pharmanex (Brisbane, Calif.). The stability and purity (>98%) of the EGCg and EC were confirmed by high performance liquid chromatographic analysis.

7.1.2. Growth of cells

HeLa (ATCC CCL2) cells were grown in 150 $cm^2$ flasks in Minimal Essential Medium (Gibco), pH 7.4, at 37° C. with 10% bovine calf serum (heat-inactivated), plus 50 mg/l gentamicin sulfate (Sigma). Cells were trypsinized with Sigma IX trypsin for 1 to 2 min and harvested by scraping and taken up in 140 mM NaCl, 5 mM KCl, 0.7 mM Na2HPO$_4$ and 25 mM Tris, pH 7.4, to a final cell concentration of 0.1 g wet weight (gww) per ml.

A mouse mammary tumor subpopulation line 4T 1 arising from a BALB/cf C3H mouse was grown in DME-10, Dulbecco's modified Eagle's medium supplemented with 5% fetal calf serum, 5% newborn calf serum, 1 mM mixed non-essential amino acids, 2 mM L-glutamine, penicillin (100 units/ml), and streptomycin (100 mg/ml) (Miller et al., 1987, Brit. J. Can. 56:561–569 and Miller et al., 1990, Invasion Metastasis 10:101–112).

7.1.3. Purification of Plasma Membranes from Cultured Cells

Cultured cells were collected by centrifugation for 6 to 15 min at 1,000 to 3,000 rpm. The cell pellets were resuspended in 0.2 mM EDTA in I mM $NaHCO_3$ in an approximate ratio of 1 ml per $10^8$ cells and incubated on ice for 10 to 30 min to swell the cells. Homogenization was with a Polytron Homogenizer for 30 to 40 sec at 10,500 rpm using a PT-PA 3012/23 or ST-probe in 7 to 8 ml aliquots. To estimate breakage, the cells were monitored by light microscopy before and after homogenization. At least 90% cell breakage without breakage of nuclei was achieved routinely.

The homogenates were centrifuged for 10 min at 175 g to remove unbroken cells and nuclei and the supernatant was centrifuged a second time at 1.4×106 g min (e.g., 1 h at 23,500 g) to prepare a plasma membrane-enriched microsome fraction. The supernatant was discarded and the pellets were resuspended in 0.2 M potassium phosphate buffer in a ration of approximately 1 ml per pellet from $5\times10^8$ cells. The resuspended membranes were then loaded onto the two-phase system constituted on a weight basis. The two-phase system contained 6.4% (w/w) Dextran T-500 (Pharmacia), 6.4% (w/w) Polyethylene Glycol 3350 (Fisher), and 5 m-M potassium phosphate, pH 7.2 (Morréand Morré, 1989, BioTechniques 7:946–958). The homogenate (1 g) was added to the two-phase system and the weight of the system was brought to 8 g with distilled water. The tubes were inverted vigorously for 40 times in the cold (4° C.). The phases were separated by centrifugation at 750 rpm (150×g) in a Sorvall HB 4 rotor for 5 min. The upper phases were withdrawn carefully with a Pasteur pipette, divided in half and transferred into 40 ml plastic centrifuge tubes. The tube contents were diluted with cold 1 mM $NaHCO_3$ and collected by centrifugation at 10,000×g in a HB rotor for 30 min. Plasma membrane pellets were resuspended in 50 mM Tris-Mes buffer (pH 7.2) and stored at –70° C. Proteins were determined using the bicinchoninic acid (BCA) assay (Smith et al., 1985, Anal. Biochem. 100:76–85) with bovine serum albumin as standard. The upper phase, enriched in plasma membranes, was diluted 5-fold with 1 mM sodium bicarbonate and the membranes are collected by centrifugation. The purity of the plasma membrane was determined to be >90% by electron microscope morphometry. The yield was 20 mg plasma membrane protein from $10^{10}$ cells.

7.1.4. Spectrophotometric Assay of NADH Oxidase

NADH oxidase activity was determined as the disappearance of NADH measured at 340 nm in a reaction mixture containing 25 mM Tris-Mes buffer (pH 7.2), 1 mM KCN, and 150 mM NADH at 37° C. Activity was measured using a Hitachi U3210 spectrophotometer with stirring and continuous recording over two intervals of 5 min each. A millimolar extinction coefficient of 6.22 was used to determine specific activity.

7.2. Results 7.2.1. Effect of EGCg and EC on Solubilized NOX Mixtures of EGCg with EC were tested first with a NOX preparation solubilized from HeLa cells (FIG. 7) and subsequently with cells. With the solubilized NOX protein, maximum inhibition was achieved by a mixture of $10^{-9}$ M EGCg plus $5\times10^{-6}$ M EC. Neither EC alone (up to and including $10^{-4}$ M) nor $10^{-9}$ M EGCg were effective in inhibiting the activity of the solubilized plasma membrane NADH oxidase protein.

Apoptosis was considerably enhanced by the combination of EGCg and EC (FIG. 8). In the absence of EC, 50% growth arrest by EGCg was observed at $10^{-5}$ M. However, in the presence of $10^{-4}$ M EC, the concentration of EGCg for 50% growth arrest was lowered to $10^{-7}$ M and, in one experiment, the cells were totally killed by the combination of $10^{-7}$ M EGCg plus $10^{-4}$ M EC.

7.2.2. Effect of EGCg and EC on NOX in Intact Cells

A similar response was seen with the NADH oxidase activity of intact 4T1 cells (FIG. 9). With $10^{-4}$ M EC, $10^{-7}$ M EGCg, or no addition, the response was minimal. However, in the presence of $10^{-7}$ M EGCg, a substantial dose response to EC was observed.

Mouse 4T1 mammary carcinoma cells are particularly refractory to drug-induced growth inhibition and cell killing. However in the presence of the combination of $10^{-7}$ M EGCg and $10^{-4}$ M EC, the cells were killed (Table 2). This remarkable drug response was reflected in the inhibition of the oxidation of NADH by the intact 4T 1 cells (Table 3, FIG. 9). The activity was completely inhibited back to basal levels by $10^{-7}$ M EGCg plus $10^{-4}$ M EC. The $EC_{50}$ for inhibition of the drug-responsive component of the plasma membrane NADH oxidase was $2\times10^{-9}$ M in the presence of $10^{-4}$ M EC alone, $10^{-7}$ M EGCg alone or $10^{-4}$ M EC+$10^{-7}$ M EGCg, the $EC_{50}$ for inhibition by EC was between $2\times10^{-9}$ M and $5\times10^{-8}$ M (Table 3).

TABLE 2

Killing of 4T1 metastatic mouse mammary cancer cells in culture.

| Addition | Increase in cell number cm$^{-2}$ over 72 h · 10$^2$ |
|---|---|
| None | 550 |
| EGCg $10^{-7}$ M | 520 |
| EC $10^{-4}$ M | 560 |
| EGCg $10^{-7}$ M + EC $10^{-4}$ M | −40* |

*100% Dead

TABLE 3

Preliminary Animal Study. Balb/c mice, 4T1 mouse mammary cancer. Treated for 5 days.

| Treatment | Amount/animal | Tumor wt (g) | Metastases to axillary nodes (Number of mice) | Lung Mets |
|---|---|---|---|---|
| Control (water only) | — | 2.3 ± 0.3 | +++ | + |
| Glaucarubolone ($4 \times 10^{-6}$ M) | 1 mg | 1.5 ± 0.1 | +++ | + |
| EGCg $10^{-7}$ M + EC $10^{-4}$ M | 0.2 + 1.2 mg | 0.75 ± 0.35 | + | — |
| Glaucarubolone + EGCg + EC | 1 + 0.2 + 1.2 mg | 1.2 ± 0.4 | +++ | +* |

Each animal received 100 ml/day
*One animal with liver metastases

Epicatechin alone was largely without effect on the cell surface NADH oxidase of 4T-1 cells (FIG. 9, no addition) over the range $10^{-7}$ M to $10^{-4}$ M. However, in the presence of $10^{-7}$ M EGCg, the drug responsive component of the cell surface NADH oxidase was inhibited maximally at about $10^{-4}$ M with an $EC_{50}$ of about $2\times10^{-7}$ M. The effect of EGCg was approximately the same as the concentration is increased up to $10^{-4}$ M (Table 4). The $EC_{50}$ was increased slightly at $10^{-5}$ and $10^{-4}$ M EGCg although the difference is not significant. The forms of the dose response curves including maximum inhibition were unchanged from that with $10^{-7}$ M EGCg and only a function of the concentration of EC (FIG. 10).

TABLE 4

$EC_{50}$ for (−)-epicatechin in the presence of varying concentrations of EGCg alone supplied as Tegreen ™ on the inhibition of tNOX activity of intact 4T1 mouse mammary cells in culture.

| | $EC_{50}$ for tNOX inhibition by (−)-epicatechin, $10^{-6}$ M | |
|---|---|---|
| EGCg concentration, M | EGCg | Tegreen ™ |
| 0 | No effect | No effect |
| $10^{-8}$ | No effect | No effect |
| $10^{-7}$ | 0.2 ± 0.1 | No effect |
| $10^{-6}$ | 0.15 ± 0.05 | 0.5 ± 0.4 |
| $10^{-5}$ | 0.7 ± 0.3 | 0.4 ± 0.1 |
| $10^{-4}$ | 0.5 ± 0.4 | 0.3 ± 0.2 |

7.2.3. Effect of Tegreen™ on NOX in Intact Cells

With a commercially supplied tea concentrate (Tegreen™, Pharmanex, Brisbane, Calif.), results were similar except that on an EGCg basis a higher concentration of Tegreen™ was required to achieve the same response (Table 4). With Tegreen™, an EGCg equivalent concentration of $10^{-6}$ M was required to elicit the response and $10^{-7}$ M was largely without effect or slightly stimulatory (FIG. 11, upper curve). Tegreen™ alone tended to stimulate the surface NADH oxidase activity of the intact 4T1 cells but the dose response with respect to EC was similar to that when EGCg in the absence of other tea constituents was added (FIG. 11, lower curve). The $EC_{50}$ for inhibition of activity by EC was $0.4\pm0.1\times10^{-7}$ M comparing $10^{-6}$, $10^{-5}$ and $10^{-4}$ M EGCg supplied as Tegreen™ (Table 4).

With intact HeLa cells, the tNOX activity was maximally inhibited at $10^{-7}$ M to $10^{-6}$ M (FIG. 12). At $10^{-5}$ M EGCg or higher, NOX activity was stimulated. (−)-Epicatechin (EC) alone is without effect on NOX activity of HeLa cells (FIG. 13, upper curve). However, in the presence of $10^{-7}$ M EGCg, a further inhibitory response to EC was noted.

It should be noted that the formulation of Tegreen™ is an old formulation which is not encompassed within the scope of this invention. It should also be noted that the data suggested by the Tegreen™ experiments indicates that combinations of catechins are therapeutically more effective than EGCg alone on tNOX inhibition.

EXAMPLE

Synergistic Interaction of Different Tea Catechins with (−)-Epigallocatechin Gallate on Inhibition of Cell Surface NADH Oxidase (NOX) Activity and Growth of 4T1 Mouse Mammary Cells in Culture 8.1. Materials and Methods 8.1.1. Chemicals The (−)-epigallocatechin gallate (EGCg), (−)-epicatechin (EC), gallocatechin gallate (GCG) and±catechin were purchased from Sigma (St. Louis, Mo.) or purified from leaves of green tea and supplied by Pharmanex (Brisbane, Calif.). The (−)-epigallocatechin (EGC) and (−)-epicatechin gallate (ECG) were purified from leaves of green tea and supplied by Pharmanex (Brisbane, Calif.). The stability and purity (>90%) of the catechins were confirmed by high performance liquid chromatographic analysis.

8.1.2. Growth of cells.

A mouse mammary tumor subpopulation line 4T1 arising from a BALB/cf C3H mouse (14, 15) was grown in DME-10, Dulbecco's modified Eagle's medium supplemented with 5% fetal calf serum, 5% newborn calf serum, 1 mM mixed non-essential amino acids, 2 mM L-glutamine, penicillin (100 units/ml), and streptomycin (100 mg/ml).

8.1.3. Spectrophotometric assay of NADH oxidase

NADH oxidase activity was determined as the disappearance of NADH measured at 340 nm in a reaction mixture containing 25 mM Tris-Mes buffer (pH 7.2), 1 mM KCN, and 150 mM NADH at 37° C. Activity was measured at 340 nm with reference at 430 nm using an SLM Aminco DW-2000 spectrophotometer (Milton Roy, Rochester, N.Y.) in the dual beam mode of operation with stirring and continuous recording over two intervals of 5 min each. A millimolar extinction coefficient of 6.22 was used to determine specific activity.

8.2. Results 8.2.1. Effect of Catechin Combinations on NOX in Intact Cells

Mixtures of EGCg with other catechins and mixtures of other catechins were tested for inhibition of tNOX activity intact with 4T1 mouse mammary carcinoma cells. Previously, maximum inhibition of the tNOX activity component was achieved by a mixture of $10^{-7}$ M EGCg plus $10^{-5}$ to $10^{-4}$ M EC. Neither EC alone (up to and including $10^{-4}$ M) nor EGCg (up to and including $10^{-6}$ M) were effective in inhibiting the residual CNOX activity of the cells.

8.2.2. Effect of EGCg and EC on NOX in Intact Cells

These findings were extended to a more detailed comparison of different concentrations of EGCg in the presence of 0, $10^{-8}$, $10^{-6}$ and $10^{-4}$ M EC on the NOX activity of the 4T1 cells (Table 5). In the absence of EC, the $EC_{50}$ for tNOX inhibition by EGCg was about $10^{-8}$ M with >90% inhibition at $10^{-7}$ M. In the presence of $10^{-8}$ EC EGCg inhibition was little enhanced. However with both $10^{-6}$ and $10^{-4}$ M EC, the efficacy of EGCg inhibition was enhanced 10-fold or greater (Table 5). EC alone was largely without effect on tNOX activity of the 4T1 cells.

TABLE 5

$EC_{50}$ and $EC_{>90}$ for (−)-epigallocatechin gallate (EGCg) in the presence of varying concentrations of (−)-epicatechin (EC) on the inhibition of tNOX activity of intact cultured 4T1 mouse mammary carcinoma cells.

| EC concentration, M | tNOX inhibition by (−)-epigallocatechin gallate (EGCg), M | |
|---|---|---|
| | $EC_{50}$ | $EC_{>90}$ |
| 0 | $10^{-8}$ | $10^{-7}$ |
| $10^{-8}$ | $10^{-8}$ | $10^{-7}$ |
| $10^{-6}$ | $10^{-9}$ | $10^{-8}$ |
| $10^{-4}$ | $5 \times 10^{-10}$ | $10^{-8}$ |

8.2.3. Effect of Other Catechins and EGCg on NOX in Intact Cells

Several catechins and catechin mixtures were tested for their ability to replace the EC in the combination with $10^{-7}$ M EGCg. ECG (FIG. 14) and EGC (FIG. 15) both were effective in enhancing the inhibition by EGCg of tNOX activity of cultured 4T1 cells. The residual tNOX activity remaining after $10^{-7}$ M EGCg was inhibited 50% by $5 \times 10^{-7}$ and $10^{-6}$ M of ECG and EGC respectively (Table 6).

Gallocatechin gallate (GCG) (FIG. 16) was less effective due to a propensity of the GCG to stimulate activity as the concentrations of GCG exceeded $10^{-7}$ M in the mixture.

Catechin was largely without effect on the cell surface NADH oxidase of 4T1 cells over the range $10^{-7}$ M to $10^{-4}$ M both in the presence (FIG. 17) or absence (not shown) of $10^{-7}$ M EGCg. Unlike GCG, catechin did not stimulate NOX activity and therefore, may represent an activity-neutral catechin component. A mixture of equal parts of ECG, EGC, EC and catechin (FIG. 18) was approximately equivalent in effectiveness to EC, ECG or EGC alone. There appeared to be no marked enhancement of inhibition by the mixture compared to the individual components tested singly (Table 6).

TABLE 6

Estimated $EC_{50}$ and $EC_{>90}$ for different catechins and catechin mixtures in the presence of (−)-epigallocatechin gallate (EGCg) on the inhibition of the residual tNOX activity of intact cultured 4T1 mouse mammary carcinoma cells remaining after addition of 0.1 mM EGCg.

| | Inhibition of residual tNOX remaining in the presence of $10^{-6}$ M EGCg | |
|---|---|---|
| Catechin | $EC_{50}$ | $EC_{>90}$ |
| Epicatechin gallate (ECG) | $5 \times 10^{-7}$ M | $10^{-6}$ M |
| Epigallocatechin (EGC) | $10^{-7}$ M | $10^{-5}$ M |
| Gallocatechin gallate (GCG) | Not reached due to stimulation | |
| Catechin (C) | Not reached due to lack of inhibition | |
| ECG + EGC + EC + C | $5 \times 10^{-7}$ M | $10^{-5}$ M |
| Base-cleaved Tegreen ™ | $<10^{-7}$ M | $10^{-7}$ M |

8.2.4. Effect of Tegreen™ on NOX in Intact Cells

When a commercially supplied tea concentrate (Tegreen™, Pharmanex, Brisbane, Calif.), was treated with NADH to cleave the gallate esters, results were similar (FIG. 19) except that on an EGCg basis less catechin was required to achieve the same response as compared to individual catechins (Table 6). With the hydrolyzed Tegreen™, >90% inhibition was achieved at an EGCg equivalent concentration of $10^{-7}$M and with an $EC_{50}$ of less than $10^{-7}$ M. The hydrolyzate was largely without effect on CNOX. A control preparation containing an amount of NaCl equivalent to the salt concentration of the tNOX hydrolyzate was without effect on activity (not shown).

In this Example, the synergy in inhibition of tNOX activity of cultured 4T1 mouse manmary carcinoma cells between the most potent tea catechin EGCg and less potent tea catechins such as EC was confirmed. Additionally, an equivalency among the catechins (EC, EGC, ECG) in eliciting the synergistic response has been shown, which is of considerable importance in efforts to optimize tea catechin mixtures for use in cancer therapy.

The present invention is not to be limited in scope by the specific embodiments described herein. Indeed, various modifications of the invention in addition to those described will become apparent to those skilled in the art from the foregoing description and accompanying figures. Such modifications are intended to fall within the scope of the appended claims.

9. EXAMPLE

Preparation of Catechins with Reduced Levels of EGCg

9.1. Materials

The green tea extract utilized was Tegreen97 from Pharmanex (Brisbane, Calif.). Tannase was obtain from Kikkoman Corp. (Japan). HPLC grade acetonitrile, methanol, and ethanol were obtained from Burdick and Jackson Labs. Inc. (USA). Analytical grade chloroform, formic acid, $NaH_2PO_4$, $Na_2HPO_4$ and $K_2HPO_4$ were obtained from Sigma (St. Louis, Mo.). Sephadex LH-20 resin was obtained from Amersham Pharmacia Biotech (UK).

9.2. Methods

Initial levels of the catechins in the green tea extract were determined by High Pressure Liquid chromatography (HPLC) using aqueous acetonitrile as a effluent. 37.5 mg of tannase and 205.3 mg of green tea extract were transferred to a 250 ml erlenmeyer flask. 100 ml buffer solution (0.2M $NaH_2PO4$–0.05M $K_2HPO_4$), with a pH between 6.0 and 6.2, was added to the flask. The flask was heated to 38–40° C. for 30 minutes in a shaker bath.

Alternately, immobilized tannase was used for the incubation step. The modified resin was prepared by immersing a macroporpus polystyrene anion exchange resin in a 0.002 M buffer of $NaH_2PO_4$ and $Na2HPO_4$ with a pH of 6.8. 4g of resin (wet weight) was added into 40 ml of 2.5% glutaraldehyde solution. The glutaraldehyde-resin solution was stirred for two hours at room temperature. The modified resin was washed with water. 4 g of tannase was dissolved in 20 ml of buffer at pH 6.8 to which the modified resin was added. The reaction was stirred at room temperature over night. Excess enzyme was washed out with buffer.

The activated resin with immobilized tannase was placed in a packed-bed reactor. A 0.5% solution of green tea extract in buffer of pH 6.8 was eluted with buffer on the packed-bed reactor at a flow rate of 0.1 ml/min.

The resultant solution from the incubation step was evaporated under a vacuum to obtain a residue of a volume of approximately 2 ml. The residue was extracted with 10 ml of ethyl acetate. The ethyl acetate was separated and put aside. The ethyl acetate extract was repeated. The aliquots of ethyl acetate were combined and evaporated under a vacuum. This process resulted in a residue called Product 1.

70 mg of Product 1 was dissolved in 1 ml of 90% ethanol and applied to a Sephadex LH-20 column. The column was eluted with 90% ethanol. Fractions of 2.5 ml were collected with a flow rate of 0.5 ml/min. The fractions were examined using TLC (chloroform:methanol:formic acid 9.0:1.0:0.2). Fractions 27 to 36 of 80 total fractions contained gallic acid. The remaining fractions, i.e. Fraction 1–26 and 37–80, were combined and evaporated to dryness. This process resulted in a residue called Product 2.

9.3. Results

The above method of incubation, extraction and separation gave the results listed in Table 7. On the first line of the table, the percentages of catechins are shown for the raw green tea extract before incubation. On the second line of the table, the percentage of catechins are shown for the solution after incubation and extraction, i.e. of Product 1. On the third line of the table, the percentages of catechins are shown after separation using liquid chromatography, i.e. Product 2.

TABLE 7

Percentage Ratio of Catechins after Treatment with Tannase

| Material | % GC | % EGC | % C | % EC | % EGCg | % GCg | % ECg | % Catechins | EC/EGCg |
|---|---|---|---|---|---|---|---|---|---|
| Raw material | 1.89 | 3.16 | 1.83 | 6.67 | 36.2 | 6.64 | 15.4 | 71.8 | 0.184 |
| Product 1 | 6.67 | 31.4 | 3.37 | 19.0 | 0.04 | 0.31 | 0.06 | 60.8 | 475 |
| Product 2 | 8.23 | 40.7 | 2.12 | 19.9 | — | 0.36 | 0.17 | 71.4 | >1000 |

What is claimed is:

1. A pharmaceutical composition comprising an effective amount of tea catechins to inhibit and/or treat cancer in a mammal, wherein said tea catechins are from green tea and the ratio of EC to EGCg concentration is about 10:1, and a pharmaceutically acceptable carrier.

2. The pharmaceutical composition of claim 1 wherein gallic acid has been removed.

3. A pharmaceutical composition comprising an effective amount of tea catechins to inhibit and/or treat cancer in a mammal, wherein said tea catechins are from green tea and the ratio of EC to EGCg concentration is about 100:1, and a pharmaceutically acceptable carrier.

4. The pharmaceutical composition of claim 3 wherein gallic acid has been removed.

5. A pharmaceutical composition comprising an effective amount of tea catechins to inhibit and/or treat cancer in a mammal, wherein said tea catechins are from green tea and the ratio of EC to EGCg concentration is about 1000:1, and a pharmaceutically acceptable carrier.

6. The pharmaceutical composition of claim 5 wherein gallic acid has been removed.

7. The composition of any one of claims 1 to 6 wherein the composition is formulated as an oral preparation.

8. The composition of claim 7 wherein the oral preparation comprises tablets, capsules, gelcaps, or powders.

9. The composition of any one of claims 1 to 6 wherein the composition is a tablet or a capsule and the pharmaceutically acceptable carrier is a binding agent, filler, lubricant, disintegrant, or a wetting agent.

10. A dietary or nutritional supplement comprising an effective amount of tea catechins to inhibit and/or treat cancer in a mammal, wherein said tea catechins are from green tea and the ratio of EC to EGCg concentration is about 10:1, and an ingestable carrier.

11. The supplement of claim 10 wherein gallic acid has been removed.

12. A dietary or nutritional supplement comprising an effective amount of tea catechins to inhibit and/or treat cancer in a mammal, wherein said tea catechins are from green tea and the ratio of EC to EGCg concentration is about 100:1, and an ingestable carrier.

13. The supplement of claim 12 wherein gallic acid has been removed.

14. A dietary or nutritional supplement comprising an effective amount of tea catechins to inhibit and/or treat cancer in a mammal, wherein said tea catechins are from green tea and the ratio of EC to EGCg concentration is about 1000:1, and an ingestable carrier.

15. The supplement of claim 14 wherein gallic acid has been removed.

16. The supplement of any one of claims 10 to 15 wherein the supplement is formulated as an oral preparation.

17. The supplement of claim 16 wherein the oral preparation comprises tablets, capsules, gelcaps, or powders.

18. The supplement of any one of claims 10 to 15 wherein the supplement is a tablet or a capsule and the ingestible carrier is an ingestible sale, a charged matrix, or an uncharged matrix.

* * * * *